United States Patent
D'Antonio et al.

(10) Patent No.: US 8,348,907 B2
(45) Date of Patent: Jan. 8, 2013

(54) HYPODERMIC INJECTION SYSTEM

(75) Inventors: Nicholas F. D'Antonio, Tully, NY (US); Richard O. Colvin, Baldwinsville, NY (US); Linda F. D'Antonio, Syracuse, NY (US)

(73) Assignee: D'Antonio Consultants International Inc., E. Syracuse, NY (US)

( * ) Notice: Subject to any disclaimer, the term of this patent is extended or adjusted under 35 U.S.C. 154(b) by 1569 days.

(21) Appl. No.: 11/821,712

(22) Filed: Jun. 25, 2007

(65) Prior Publication Data

US 2008/0015512 A1    Jan. 17, 2008

Related U.S. Application Data

(62) Division of application No. 10/224,034, filed on Aug. 20, 2002, now Pat. No. 7,235,063.

(60) Provisional application No. 60/313,978, filed on Aug. 21, 2001, provisional application No. 60/358,861, filed on Feb. 22, 2002.

(51) Int. Cl.
*A61M 5/00* (2006.01)
(52) U.S. Cl. .......................................... 604/232; 604/235
(58) Field of Classification Search .................. 604/181, 604/187, 232–234, 218–231, 61–69
See application file for complete search history.

(56) References Cited

U.S. PATENT DOCUMENTS

| | | | |
|---|---|---|---|
| 1,943,120 | A | 1/1934 | Kabnick |
| 2,573,954 | A | 11/1951 | Casson |
| 2,653,603 | A | 9/1953 | Hein, Jr. |
| 3,899,298 | A | 8/1975 | Szczesniak |
| 4,687,465 | A * | 8/1987 | Prindle et al. .............. 604/61 |
| 4,693,706 | A | 9/1987 | Ennis, III |
| 5,026,343 | A | 6/1991 | Holzer |
| 5,304,128 | A | 4/1994 | Haber et al. |
| 5,318,522 | A | 6/1994 | D'Antonio |
| 5,360,410 | A | 11/1994 | Wacks |
| 5,599,316 | A | 2/1997 | Blakely |

(Continued)

FOREIGN PATENT DOCUMENTS

DE    688 650    2/1940

(Continued)

*Primary Examiner* — Kevin C Sirmons
*Assistant Examiner* — Phillip Gray
(74) *Attorney, Agent, or Firm* — D. Peter Hochberg; Sean F. Mellino; Daniel J. Smola

(57) ABSTRACT

A hypodermic injection system particularly for use in mass immunizations having a handpiece with a grasping mechanism for holding ampules filled with injectate, a plunger for driving into the ampule to discharge the injectate in an injection process, an injection spring mechanism for driving the plunger, a motor and/or manual mechanism for cocking the injection spring mechanism, and an ampule ejection mechanism for ejecting ampules after use under control of a release mechanism. Ampules can be loaded, used and ejected without contact by the user of the system or the patient being injected. Also disclosed are a filling station for filling ampules through their injection orifices, and an arming device for setting the injection spring. Ampules are disclosed having a piston which is drivable towards an orifice to discharge injectate through the orifice. Ampules are also disclosed having enlarged proximal portions for easy grasping by the grasping mechanism of the injector. Ampules are further disclosed with separators for mixing lyophilized medication and a diluent. Further disclosed are magazines for holding ampules for sequential use by the hypodermic injector. The disclosed system finds particular use as a mass immunization kit for making numerous injections in the field.

27 Claims, 24 Drawing Sheets

U.S. PATENT DOCUMENTS

| | | |
|---|---|---|
| 5,743,431 A | 4/1998 | Brattesani |
| 5,782,802 A | 7/1998 | Landau |
| 5,823,998 A | 10/1998 | Yamagata |
| 5,875,976 A | 3/1999 | Nelson et al. |
| 5,891,086 A | 4/1999 | Weston |
| 5,938,637 A | 8/1999 | Austin et al. |
| 5,950,832 A | 9/1999 | Perlman |
| 5,992,634 A | 11/1999 | Woodring et al. |
| 6,056,716 A * | 5/2000 | D'Antonio et al. ............. 604/68 |
| 6,290,680 B1 | 9/2001 | Forsberg et al. |
| 6,506,177 B2 | 1/2003 | Landau |
| 6,520,928 B1 | 2/2003 | Junior |
| 6,682,504 B2 | 1/2004 | Nelson et al. |
| 6,719,141 B2 | 4/2004 | Heinz et al. |

FOREIGN PATENT DOCUMENTS

| | | |
|---|---|---|
| DE | 199 55 201 | 5/2001 |
| EP | 0288443 | 10/1988 |
| EP | 0518561 | 12/1992 |
| GB | 789826 | 1/1958 |
| GB | 1140299 | 1/1969 |
| WO | WO 98/28030 | 7/1998 |
| WO | WO 99/17820 | 4/1999 |
| WO | WO 00/35520 | 6/2000 |
| WO | WO 00/40284 | 7/2000 |
| WO | WO 01/32255 | 5/2001 |
| WO | WO 01/47584 | 7/2001 |

\* cited by examiner

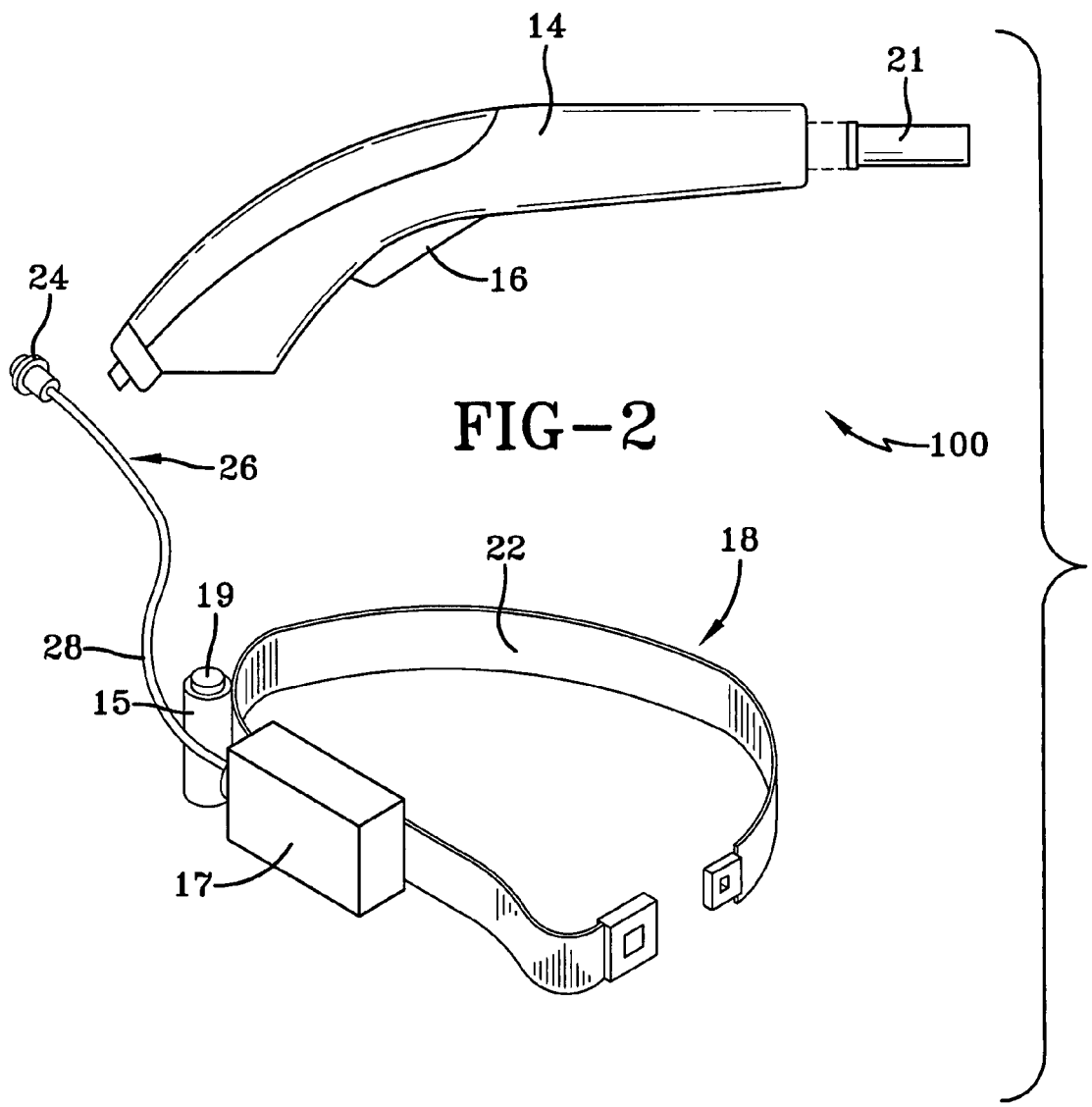
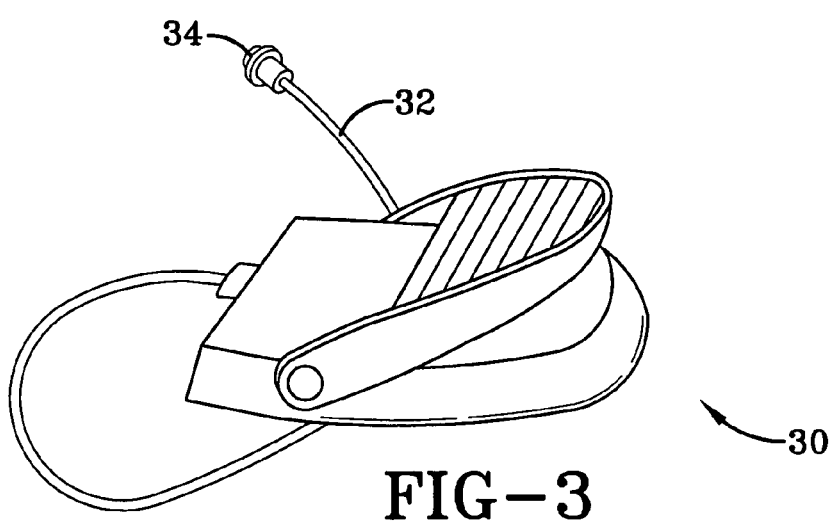

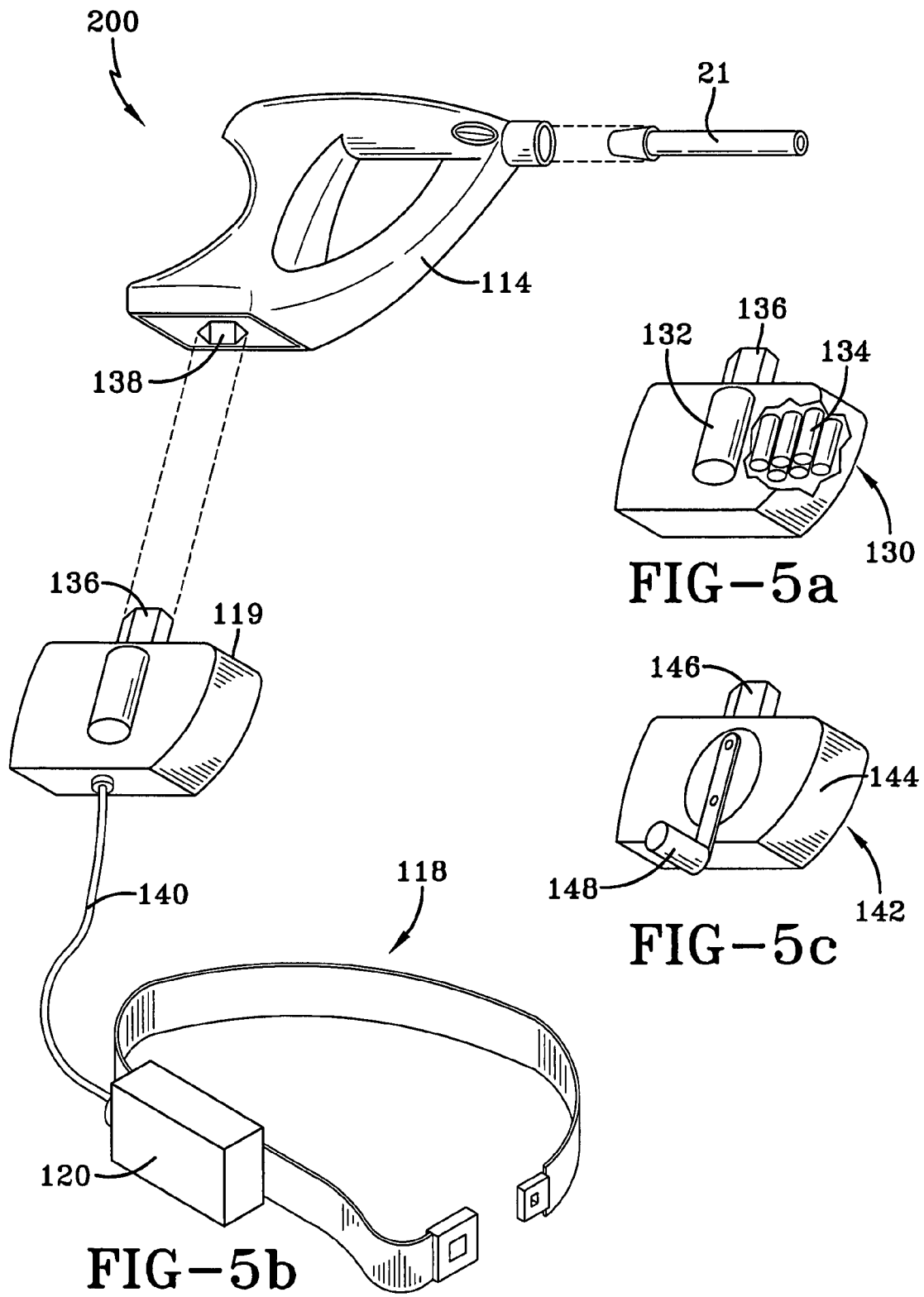

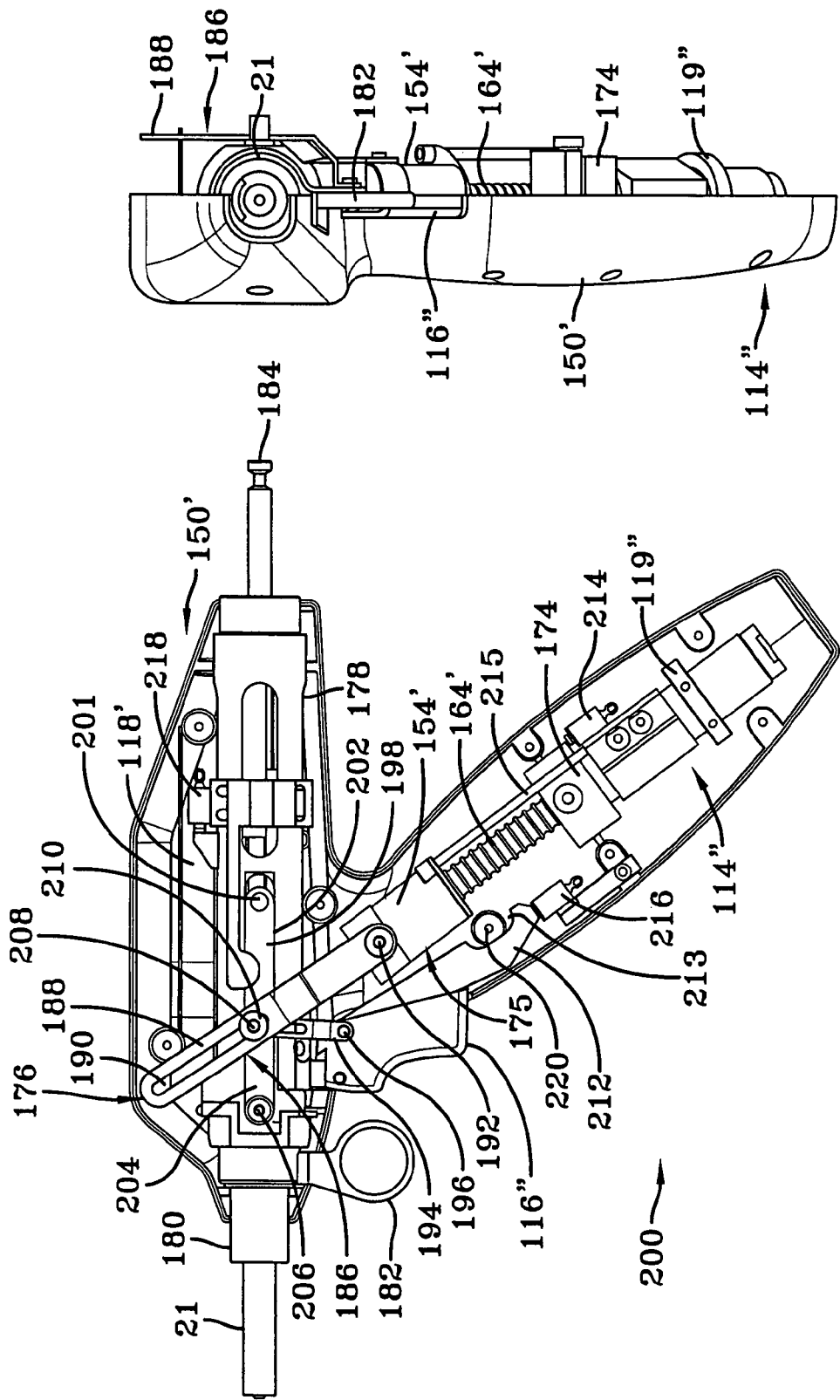

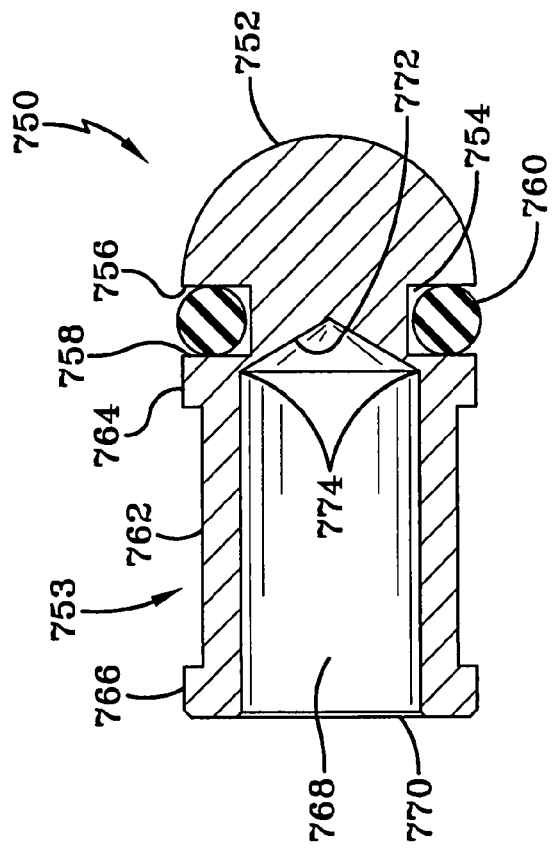
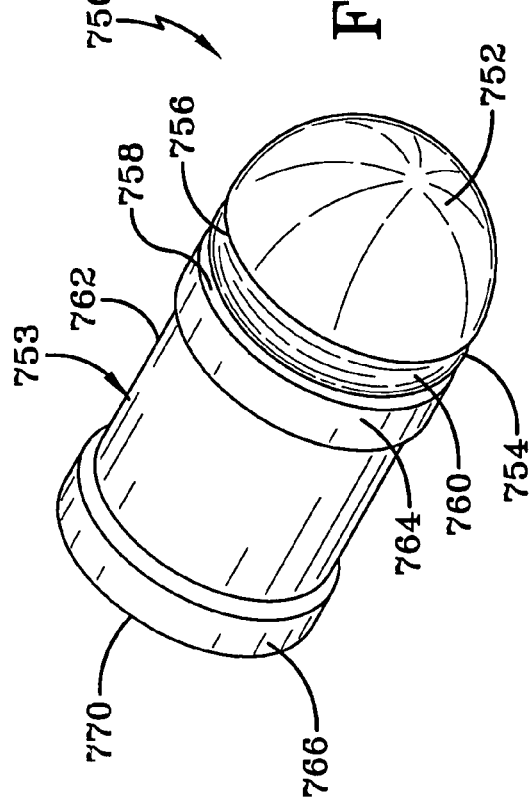
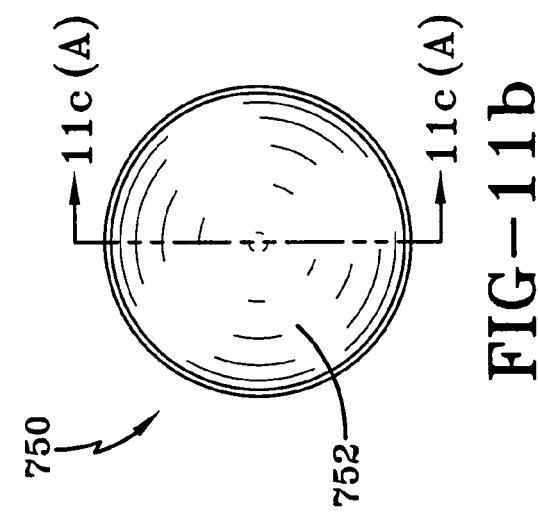

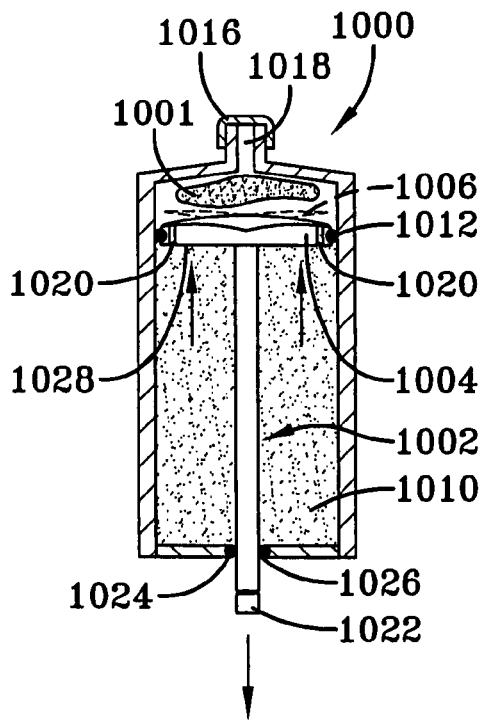
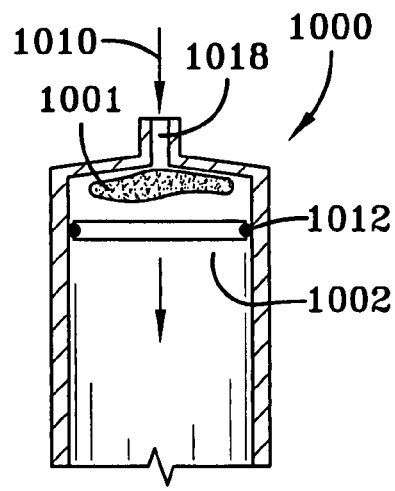
FIG-20a  FIG-20b
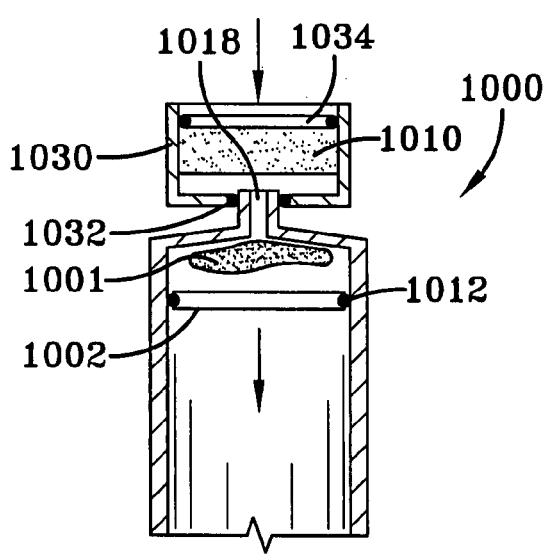
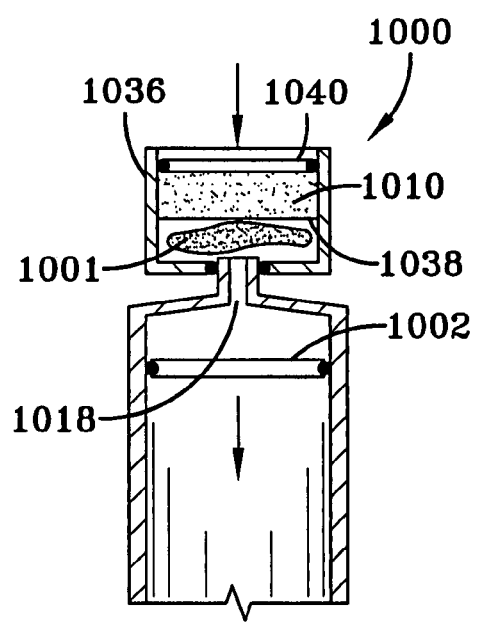
FIG-20c  FIG-20d

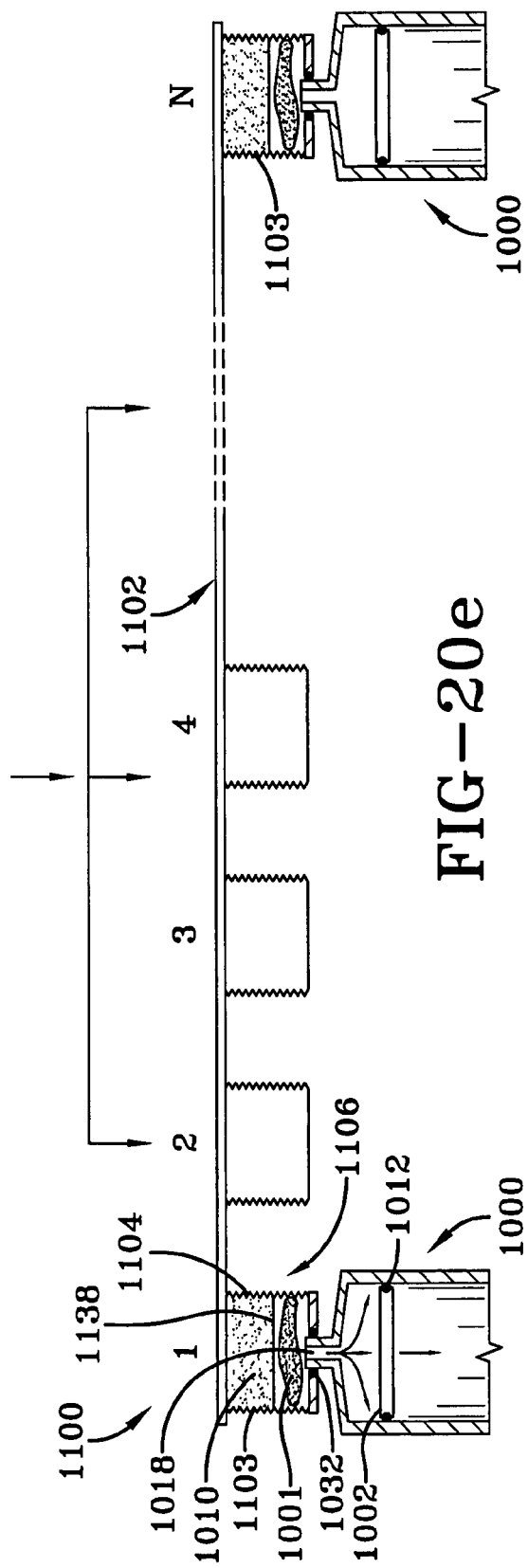
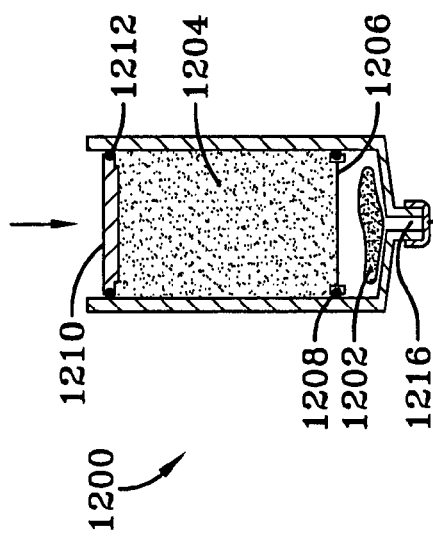

HYPODERMIC INJECTION SYSTEM

CROSS REFERENCE TO RELATED APPLICATIONS

This application is a division of U.S. patent application Ser. No. 10/224,034 filed Aug. 20, 2002, and claims the benefit of U.S. provisional patent applications Ser. No. 60/313,978 filed Aug. 21, 2001 and Ser. No. 60/358,861 filed Feb. 22, 2002.

BACKGROUND OF THE INVENTION

1. Field of the Invention

This invention relates to hypodermic injection systems, and in particular to those residing in a kit format. It more particularly relates to hypodermic injection systems in kit form for mass inoculations, using electrical or manual power. The invention additionally relates to hypodermic injection systems having ampules that are processed to avoid cross contamination.

2. Description of the Prior Art

Many forms of hypodermic injection systems are available. These systems include rapid delivery of vaccines/medications with jet injectors that utilize the same orifice for every injection, and in some cases, use individual, single use ampules that must be handled by the vaccinator when filling them with vaccine and/or when inserted or removed from the injector. Some are manually armed, these to include all personal use injectors now available, and some have other means of power such as compressed gas. None of the injection systems are available in kit form that will provide healthcare workers with everything needed to deliver thousands of shots in remote or urban locations before returning to a central location for an equipment re-supply or re-energizing the power sources, and none supply single use, self-destruct ampules in a magazine format that can also be used as a shipping container, or if needed, as a mixing structure for the simultaneous preparation of numerous lyophilized filled ampules.

Elements of this disclosure that were considered in earlier patents by at least one of the present inventors are: (1) one ampule per injection found in U.S. Pat. No. 5,080,648, (2) the magazine concept for holding ampules while connected to the injector, and a guard ring around the ampule to discourage splashing are found in U.S. Pat. No. 5,318,522, (3) inserting new ampules and/or discarding used ampules without the need of any physical contact by the user, and also the arming station for compressing an energy storage spring in the hand piece are found in PCT application Serial No. PCT/US00/07470, and (4) perforator (or mini-needle) delivery for reduced pressure and pain to the patient is found in U.S. Pat. No. 6,056,716. One of the present inventors has a pending patent application directed to a structural containment of low cost syringes used at high pressure. Elements from each of the four patents are discussed in the present disclosure for mass immunization systems, clinical injectors, and personal use injectors, and the invention herein will represent improvements or new ways for performing these vital functions for all types of injection systems. The latter patents are all incorporated herein by reference.

The invention in its preferred form provides the equipment needed for an electrically powered injection kit, including enough battery power for thousands of injections without means of support required from a central location or conventional sources of power. The basic means of energizing the injector is electrical power; however, as a user option, the kit and injection devices preferably also include a means for manual operation to assure continuation of the injection procedure if the transportable power sources are depleted and/or a source of renewable power is not available. The risk of cross-infection is avoided with disposable, single use, self-destruct ampules (also referred to as cartridges, capsules, vials, etc.) that are designed to interface with the injector in such a way that user contact with the ampules both before and after the injection is unnecessary. In addition, with respect to the preferred embodiment, the trigger is disabled until the ampule is securely held in place with the combination of a grasping jaw assembly and a locking sleeve to prevent the possibility of an ampule becoming a projectile when the injection ram is released. The ampules can be pre-filled by the manufacturer with liquid or lyophilized medication, or can be filled on site if necessary. Also included in the kit are magazines that hold numerous ampules before re-supply is needed. These magazines are designed for rapid, sterile delivery when used with the injector. In some cases, the magazine also serves as the shipping container for the ampules, and has the capability of simultaneous, on site mixing of the lyophilized filled ampules when needed. Alternatively, a filling station provides an efficient and sterile means for filling the ampules with liquid or lyophilized medication just prior to delivery.

The method for non-contact changing of ampules has utility for clinical situations and personal use injections as well, where avoiding the risk of cross infection to healthcare workers is critically important when dealing with patients harboring dangerous pathogens. By the same token, where the risk of cross infection is not a factor, such as patients receiving insulin, or perhaps the daily delivery of growth or other hormone injections, the patient or healthcare worker assisting them can easily handle the ampule for both insertion and removal with the novel grasping system disclosed. The availability of this system has special utility for people who find the prior art techniques for filling the ampule and manually arming personal-use injectors to be physically challenging, if not impossible, in some cases.

For all of the injection scenarios discussed, very short perforators (1 to 2 mm) as the exit nozzle, and used for piercing the injection site prior to jet delivery, are included in the preferred embodiment because they allow for low pressure injections (200 to 1,000 psi) as opposed to typical jet injection pressures on the order of 2,000 to 3,500 psi or more. Properly contained ampules, as discussed in the pending U.S. patent application referred to above, open the door for manufacturer-modified insulin and other syringes having 27 or 28 gauge needles that are already produced by the hundreds of millions, which when supplied at perforator length will provide an injection orifice on the order of 0.008 or 0.007 inches, which are typical diameters for jet injection systems. The economy of this approach is quite substantial.

SUMMARY OF THE INVENTION

The object of this invention is to provide a new, high-speed injection system that is economical, technically suited to campaigns for mass immunization and meets the needs of reliability, ergonomics, power availability, cost, safety and effective injections. The system is designed with several options for both powered and manual operation so that the needs of a wide variety of users can be met, these to include clinical and personal use injection systems. One option for powering the injector is an embodiment wherein a motor is remote from the handpiece discussed below, and referred to as a "Motor-Off Tool" (MOT) "Handpiece" with three methods including both electrical and manual means for compressing the injection spring. Also available is another embodiment wherein a motor is included in the handpiece, and referred to as a "Motor-In-Tool" (MIT) "Handpiece" similar to that reported in earlier disclosures by at least one of the inventors; however, according to a preferred embodiment in this disclosure, rather than a rotating cam mechanism for compressing the energy storage spring, a gear reduction and ball screw are used to do the same thing which provides novel methods and advantages for operating the motor in both the forward and reverse directions. For example, motor reversal allows for increasing the speed of rapid, repetitive injections by compressing the injection spring in one direction and then reversing direction for an immediate return to the starting point in preparation for the next arming cycle regardless of whether or not the present injection is delivered. An internal switching arrangement determines when the motor drive reaches the intended location, then provides an appropriate signal to first stop, latch the spring, and then reverse motor direction at the appropriate time. This sequence of repeated motor reversal takes place for every injection cycle, the distance of travel in each direction being determined by the volume of injectate to be delivered. In every case described, the mass immunization kit will also include a means for manual delivery if necessary; and this system has utility as a manual device for clinical situations.

In an alternate embodiment, the forward direction of the motor allows for the ball screw drive to completely eliminate the energy storage injection spring by using a direct drive delivery from the motor to the ampule piston. One of the advantages of direct drive is the ability to provide an ever-increasing drive voltage to the motor that, in turn, will yield a profile of increasing pressure over the course of an injection. This increasing pressure will drive the injectate ever deeper, rather than ever more shallow, which will discourage the inclination of medication being left on the surface as is sometime seen with the usual spring driven, orifice oriented systems. This feature is especially useful for personal use injectors used by diabetics who are often very sensitive to the correct amount of insulin entering the body. Availability of reversing motor direction can also be used for filling an empty ampule, and has particular utility with personal use injectors as an improvement to the tedious manual methods now in use. To do this, the injector ram will first grab the plunger of an empty in-dwelling ampule, and then, with a push button command by the user, the injector will pull the plunger back to draw vaccine from a supply connected to the front end of the ampule. Mechanical or magnetic means can be used to make this connection to the ampule piston. Once the ampule is full by virtue of the reverse direction, a low speed button controlled motor drive will allow the vaccinator to slowly "jog" the piston forward, and visually determine when all air is expelled from the ampule. For direct drive delivery, the motor is then transferred to its high-speed mode to drive the injectate into the injection site.

The ampules are designed for interfacing with a circular set of grasping jaws on the front of the injector. In one embodiment, the system comprises the following: (1) the ampules are packaged on a tear-away paper strip, (2) a filling station fills the ampules with pre-mixed, liquid vaccine while attached to the strip, (3) two different magazine options are available that house the ampules for rapid, easy insertion into the magazine, and then, one by one into the injector, (4) the injection is followed by self-destruction of used ampules, (5) two different handpiece options (the choice depending on user circumstances), and (6) several options for compressing the spring. The high-speed manual option mentioned earlier is an especially important feature for financially strapped countries that are unable to afford higher-level injection systems. The primary means for arming the automatic injector is electrical power for energizing a motor that serves to compress an injection spring. It should be noted that the spring-energized injector options are virtually always adaptable to manual operation as either a primary or emergency back-up system. This option is not available with conventional compressed gas, $CO_2$ or ignitable gas drive systems.

Also disclosed are means for an on site mixing of pre-filled individual ampules having lyophilized medication in one compartment, and its mixing diluent in a companion compartment, the two being separated by an appropriate barrier. Several means are shown for utilizing a barrier between the medication and its diluent. The barrier can be frangible or a one-way valve. In one embodiment, a filling station will provide sufficient force for filling the individual ampules with pre-mixed liquid vaccine through the exit nozzle, an option that is also useful for the personal use injectors described above. This approach for front end filling will virtually eliminate the problem of having air enter the chamber that usually occurs when filling ampules by creating a vacuum when drawing back on the plunger. Alternatively, the filling station can provide sufficient force to insert the diluent through the exit nozzle and then mix it with lyophilized medication located in the ampule.

A new concept of a mixing magazine allows for simultaneous, on-site mixing of an entire magazine full of the pre-filled, lyophilized/diluent cartridges. In this case, the magazine can also be used as the shipping container from the manufacturer to anywhere in the world thus, of course, lowering cost and further reducing the risk of contamination due to intermediate handling.

In summary, the system includes a transportable injection station or kit that is easily moved from place to place by foot, bicycle, motor scooter, motorcycle, water, air transport or whatever means is available for moving people and equipment to an immunization site. If no other working surface is conveniently available at the site, legs provided as part of the station are opened and extended to the proper height for the user, and optional flat panels from one to all of the four sides of the housing are extended to form a working surface if needed. When the kit is opened, the healthcare worker will have everything needed for thousands of injections without any other means of support for the amount of time expected at the location. As mentioned above, the kit will include magazines of the selected type, filling station if needed, enough battery power to provide the number of shots expected, and a module for manually arming the injector in the event that all battery power is unexpectedly depleted, and/or the power needed for recharging the batteries is not available.

BRIEF DESCRIPTION OF THE DRAWINGS

FIG. 2 is a partially exploded, pictorial view of one embodiment of the invention having a motor off the tool;

FIG. 3 is a pictorial view of a mechanical arming system for use with the embodiment shown in FIG. 2;

FIG. 5a is a pictorial view of a Motor-In-Tool injector having a removable motor and battery module for arming the Motor-In-Tool embodiment of the invention;

FIG. 5b is a pictorial view of a motor-In-Tool injector having a removable motor module for the Motor-In-Tool embodiment of the invention;

FIG. 5c is a pictorial view of a removable, back-up manual-arming module for the Motor-In-Tool embodiment of the invention;

FIG. 7a is a cut-away view of a second injector for the embodiment of the Motor-In-Tool invention depicted in FIG. 6a, showing its internal mechanism in its armed condition;

FIG. 7b is a partly cut-away front view of the injector shown in FIG. 7a also showing the internal mechanism in its armed condition;

FIG. 8b is an enlargement of the ball transfer subsystem shown in FIG. 8a

FIG. 8c is an enlargement of the jaw structure for grasping ampules as shown in FIG. 8a;

FIG. 8d is an illustration of one embodiment for self-destruction of a perforator after use in FIG. 8a;

FIG. 11a is a perspective view of an alternate embodiment of a frangible piston for use in the ampule shown in FIGS. 10a-10c;

FIG. 11b is an end view of the piston shown in FIG. 11a;

FIG. 11c is a view taken along the line A-A in FIG. 11b;

FIG. 12b is an enlargement of a portion of FIG. 12a;

FIG. 20a is a schematic view of an ampule according to the invention with a lyophilized/diluent vaccine separated by a mixing piston with a one-way valve;

FIG. 20b is a schematic view of the ampule shown in FIG. 20a with internal lyophilized vaccine and external mixing diluent being forced into the exit nozzle;

FIG. 20c is a schematic view of an ampule according to the invention with lyophilized vaccine, having an external appendage containing the mixing diluent;

FIG. 20d is a schematic view of the ampule shown in FIG. 20c having an external appendage containing both lyophilized vaccine and diluent separated by a barrier;

FIG. 20e is a schematic view of another aspect of the invention showing a magazine full of ampules, each with a collapsible storage unit; and FIG. 20f is a schematic view of another variation of an ampule according to the invention showing it with lyophilized vaccine and diluent separated by a slidable frangible barrier.

DETAILED DESCRIPTION OF THE PREFERRED EMBODIMENTS

Figure 1:
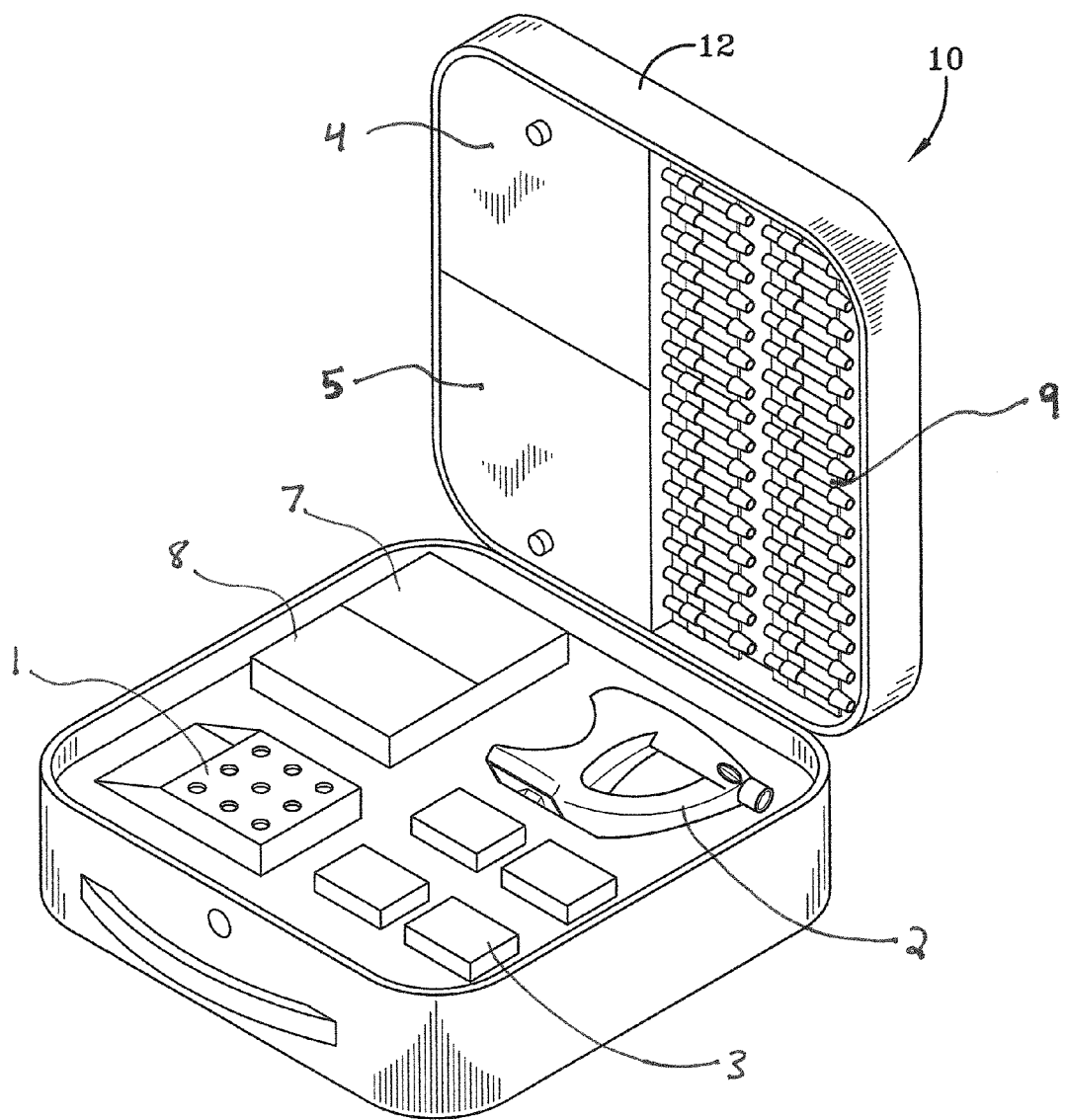
FIG. 1 is a pictorial view of a portable injection system or kit according to the invention.

FIG. 1 illustrates a customized, all-inclusive, carrying case 12 for the portable injection system, station or kit 10 according to an embodiment of the invention. Each carrying case 12 of the portable system 10 contains all components necessary for a healthcare team to efficiently administer thousands of injections at the rate of up to 600 people per hour, this equipment to include several magazines 1, at least one handpiece 2, enough battery power 3 for the number of injections expected, manual arming means 4 if needed, at least one filling system 5, several battery charging options 6 and simple tools 7 to effect repairs to the system components.

The case has retractable legs (not shown) for standing the unit in an upright position and flat panels from the four sides that can be pulled out to form a working surface (not shown) for the healthcare team if no other surfaces are available or convenient. Sterile components such as gauze, cotton balls, band-aids 8, etc., will also be housed in the case. Several ampule strips 9 should be included in the case as a fill-in or backup in case a delay occurs in the normal procedure for delivery; however, for the enormous number of inoculations needed for a mass immunization campaign, it is anticipated that the required number of ampules will be transported to the site in separate cartons and/or shipping magazines, and might even contain pre-filled liquid or lyophilized ampules.

One of the main embodiments of the invention is referred to as a "Motor-Off-Tool" or "MOT," where the electrically operated motor (discussed below) is separable from the injection device that it is driving. The injection device preferably includes a handpiece for effecting injections.

Figure 4:
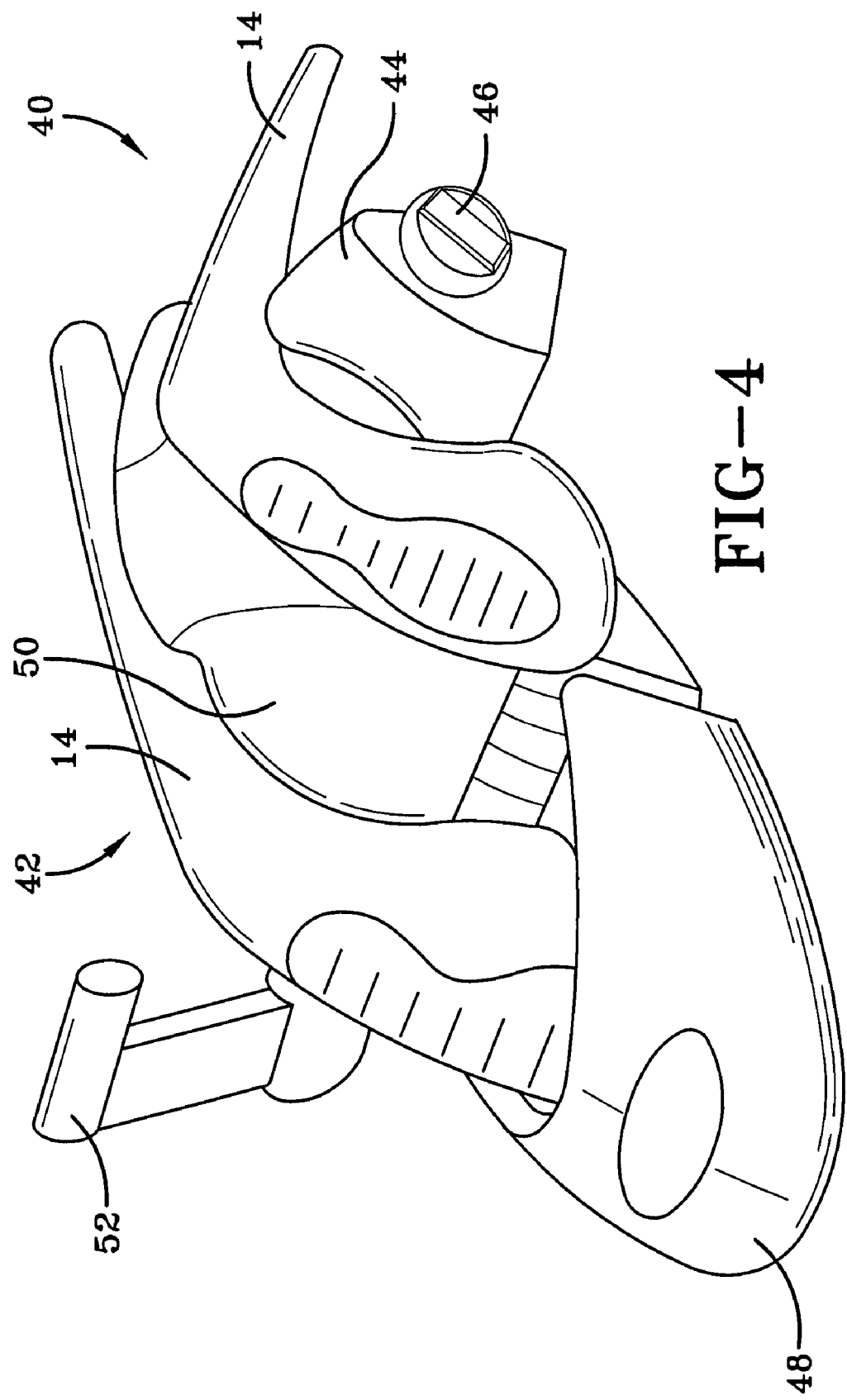
FIG. 4 is a pictorial view of an electrical or optionally manual arming station for compressing an injection spring in the embodiment shown in FIG. 2.

FIGS. 2 through 4 are illustrations of the various ways to deal with arming a Motor-Off-Tool (MOT) device, i.e., it includes a handpiece 14 containing an injection spring (discussed below) and a trigger 16, but a motor 15 and a battery 17 are on motor-battery belt assembly 18 are located off of handpiece 14. Because of this, MOT handpiece 14 is less expensive and extremely light at an estimated weight of approximately 8.5 ounces (240 g), where the handpiece is made from an appropriate plastic, and the plastic and injection spring comprising nearly all of the weight of the handpiece. The reduced weight has the added advantage of less fatigue to the healthcare worker when thousands of injections are given.

FIG. 2 shows a Motor-Off-Tool apparatus 100 having a belt-motor assembly located on a belt pack 22, arm pack or the like, and is attachable to a convenient location on the healthcare worker giving the injections. A moveable center (not visible but similar to a speedometer cable) located inside tether or cable 26 is fastened on one end to a draw rod (discussed below) on handpiece 14, and is used for applying the pulling force needed to compress an injection spring in handpiece 14, also discussed below. The outside shell of tether 26 is connected to handpiece 14 with a coupler mechanism 24. The other end of the movable center of cable 26 is attached to a motor drive 19 located on belt back 22, and this end of tether or cable 26 is attached to the housing of motor drive 19 with a coupler or connection mechanism 28. After an injection is given, a signal goes back from the handpiece to the motor control which will instruct the motor to pull on the movable center of cable 26 to again compress the spring in preparation for the next injection as explained later. The injection fluid or injectate is held in disposable ampules 21. This option allows the vaccinator to move around freely and provides for very high-speed operation, all the while requiring very little outside assistance. Mechanical tether 26 should be of adequate strength, and could be fairly stiff which, for some situations will also possibly add unwieldy weight to handpiece 14.

FIG. 3 illustrates a manually operated foot pedal assembly 30 for activating the movable center of mechanical tether 32 which functions exactly as described for tether 26 in FIG. 2 for compressing the spring in handpiece 14. The outer shell of tether 32 is connectable to handpiece 14 with coupler mechanism 34. No additional energy is needed and no motor is involved for using this foot-operated device.

FIG. 4 shows a pair of Motor-Off-Tool (MOT) injectors residing in rearming station 40; however, in this case an electrically operated arming station 42 is used. While not mandatory, the primary objective of arming station 42 is for the vaccinator and an assistant to work together, wherein the vaccinator will give the shots and the assistant will move the handpieces around as described below. Arming station 42 has a pick-up cradle 44 for holding a fully armed Motor-Off-Tool injector, and a rearming dock or port location 50 to accept an unarmed injector. Arming station 42 can be adapted to hold more than one MOT handpiece, wherein two are shown in FIG. 4 as configured for use with an assistant. Cradle 44 on arming station 42 is for holding an injector 14 that has already been armed and ready for use. A pick-up cradle adjustment knob 46 on arming station 42 is adjustable in order to place the handpiece at an angle that is most convenient and comfortable to provide access to a fully armed injector 14 for the vaccinator. Arming station 42 also has an arming station base 48 on which the aforementioned pick-up cradle 44 and a rearming dock or cradle 50 is located. In addition, base 48 also has an optional or back-up manual arming lever 52 to rearm the handpiece resting in dock or cradle 50 in the event electrical power is not available, all of which are discussed below. At the beginning of an immunization sequence, both injectors are typically unarmed. When arming cradle 50 senses the presence of handpiece 14, it pulls the injector draw rod to compress the injection spring to the latched position, as discussed hereinafter. After arming is completed, the armed handpiece is moved to pick-up cradle 44, and the second injector is placed in arming cradle 50 and armed. At this point, the vaccinator takes an armed injector from cradle 44 to give an injection and the assistant will move the second injector to pick-up cradle 44 while at the same time the vaccinator will squeeze trigger 16 of handpiece 14 to then release the injection spring, therein driving a ram in handpiece 14 to expel the jet velocity fluid from the ampule. After giving an injection, the vaccinator ejects used ampule 21 and deposits handpiece 14 into the now empty rearming cradle or dock 50, and picks up the armed handpiece 14 from cradle 44 wherein handpiece 14 is ready to retrieve a new ampule 21 for the next injection. Benefits with arming station 40 include the elimination of any kind of tether, so that the vaccinator's arm has complete freedom of movement. Also, in a campaign with an adequate supply of assisting personnel, which is often the case in mass campaigns, arming station 40 will relieve the vaccinator from all duties except for delivering injections, thus insuring an efficient, high-speed operation. If, however, a vaccinator is working with very little assistance, the arming station 40 option would require more motion and effort on the part of the vaccinator than the mechanical tether option. Also, unlike the mechanical tether option, in which the vaccinator can move around freely, this option requires the vaccinator to remain close to the arming station in order to swap handpieces 14 after each injection. The arming station concept is also conveniently applied to the personal use injector, wherein the motor and battery can be housed in a unit that also serves as a compact storage and carrying case that is easily concealed by the user, and which also makes the handpiece very compact, lightweight and easily maneuvered for a personal injection.

A second main embodiment of the invention is referred to as a "Motor-In-Tool" or "MIT," where an electric motor is plugged into or otherwise is a part of the injection device which it is driving, in this case a handpiece as described below. Referring to FIGS. 5a-5c, they show together a Motor-In-Tool device or apparatus 200 having a handpiece 114, and in the embodiment of FIG. 5b, a battery-belt assembly 118 having a battery 120, and a motor module with a motor 119.

Figure 8A:
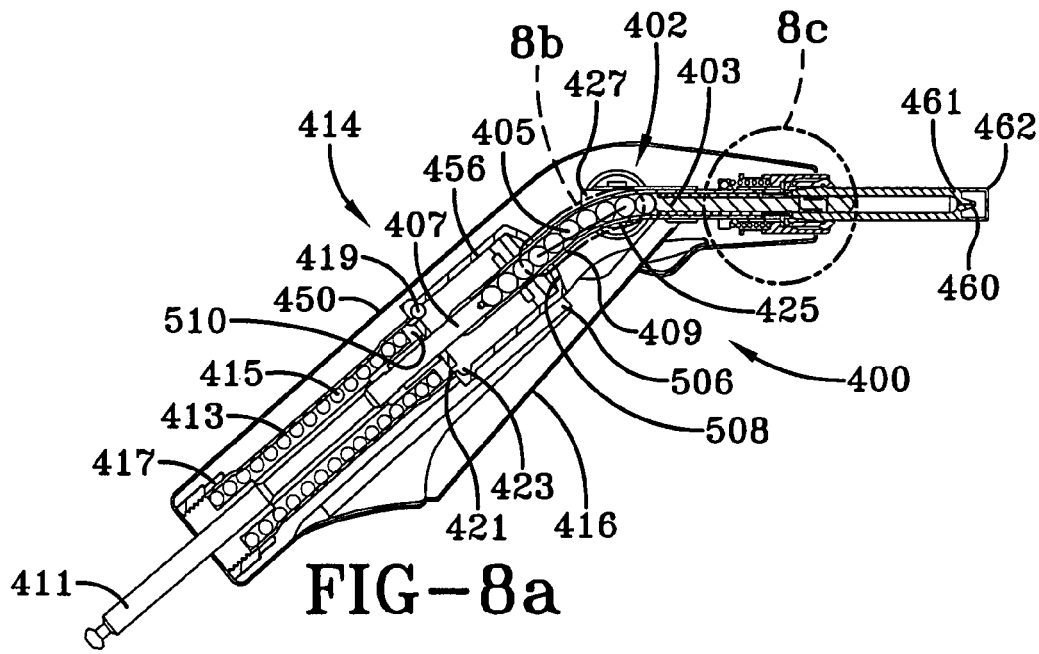
FIG. 8a is a cut-away view of a version of an injector for the first embodiment of the invention for the Motor-Off-Tool injector shown in FIG. 2 with an ampule illustrated with a perforator at the exit port.
Figures 8B, 8D:
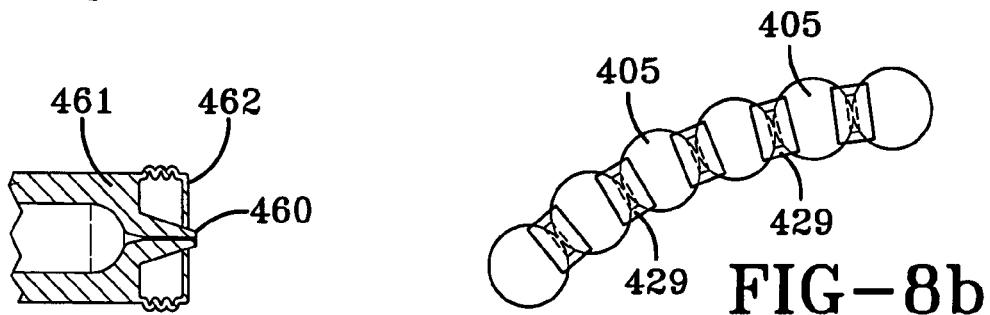
Figure 8C:
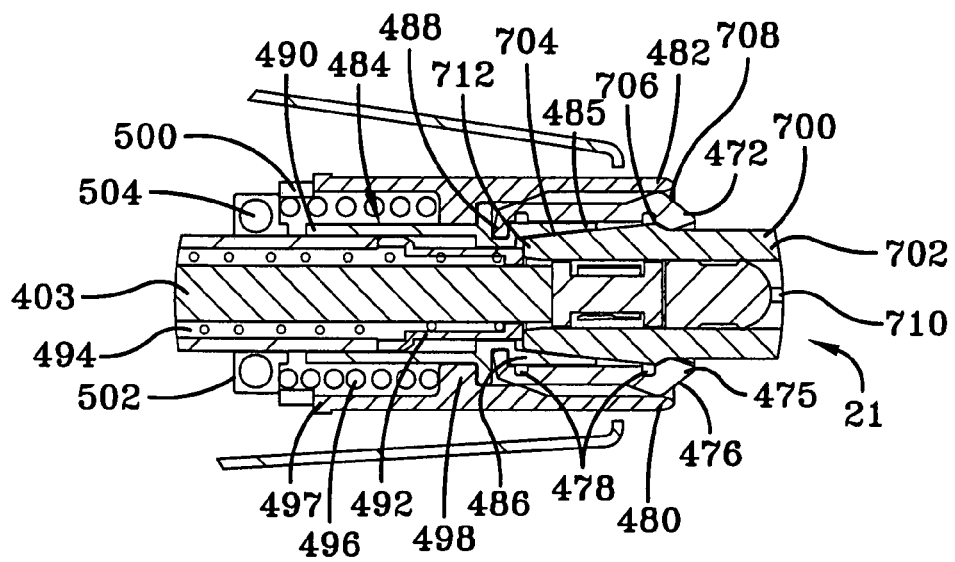

FIGS. 5a-5c illustrate various options for arming the Motor-In-Tool (MIT) injector or handpiece 114. Depending on the required shot capacity, battery 120 can be housed on handpiece 114 or in a separate off-tool compartment as shown in FIG. 5b. Just like the Motor-Off-Tool (MOT) handpiece 14, the MIT handpiece 114 houses an injection spring, the force transfer system that includes a plunger rod such as ampule plunger rod 403 as illustrated in FIGS. 8a-8c, trigger, and the ampule grip/release system as discussed in greater detail below. Thus, with reference to FIGS. 10a-10c, ampule 21 includes an injecting piston 718. Piston 718 is driven forward by plunger rod 403 to force injectable material into the intended target.

FIG. 5a illustrates a removable module 130 containing a geared down motor 132. Depending on the desired injection pressure and stroke length for a particular injector design, any number of conversion values could be used, one value implemented for this system has an armature speed as high as 13,900 revolutions per minute (RPM), but with very low torque. This high armature speed is reduced by 29:1 with an appropriate gear reduction to yield an output speed of 480 RPM to shaft 136 (8 revolutions per second), and except for an inevitable loss due to conversion efficiency, the torque output is therefore increased by the same ratio, thus providing the power needed to compress the injection spring (not shown in this figure). In this embodiment, a battery 134 is connected to the motor inside of module 130, wherein both the motor and battery are connected to the handpiece 114 during its operation by insertion of an output shaft 136 into a mating receptacle 138 on handpiece 114.

FIG. 5b illustrates a removable module that contains only the geared down motor 119 when the motor is connected to handpiece 114, but battery 118 is off the tool during operation and is connected to motor 119 with an electrical tether 140. Motor 119 has the same type motor shaft 136 as shown in FIG. 5a for insertion into receptacle 138. This is a more likely situation for providing power to handpiece 114 when thousands of injections are expected, i.e., a larger remote battery pack can be clipped onto a belt or vest, carried in a pocket, or placed on a stationary surface next to the vaccinator without the risk of excessive fatigue from constantly moving the greater weight. The MIT handpiece 114 (that is, when motor 119 is connected thereto) is estimated to weigh about 14 ounces and is somewhat larger than an MOT handpiece 114 (when motor 119 is not connected); however, it is still much lighter than any other mass campaign injector known to the inventors. The MIT handpiece 114 weighs about 14.5 to 16.5 ounces, wherein added to the 8.5-ounce MOT handpiece 114 are motor 119 at about 4 ounces and the linkage from the motor to the gears weighing from 2 to 4 ounces. The option shown in FIG. 5b provides the vaccinator full range of arm motion and complete freedom to walk around; that is, handpiece 114 does not have to be put down between injections and one-handed operation to load, inject, and eject ampules 21 is possible. While not shown, it is clear than other sources of power, such as solar or main power, when converted to the voltage needed can also be used to drive the motors in FIG. 5b.

FIG. 5c shows a module 142 for the manual arming of handpiece 114, and which is connected to the injector in the same manner as that described for the modules of FIGS. 5a and 5b. This format takes the place of the motor and the battery pack needed to energize it. Module 142 has a housing 144, and a manually driven handle 148 coupled to geared down interface prior to moving output shaft 146 which is connected to receptacle 138 on handpiece 114 during its operation. Manual arming of handpiece 114 is facilitated by rotating handle 148 several times to provoke the amount of rotation needed on output shaft 146 to compress the injection spring. While not shown in any of the figures, the MIT injector 200 can also be manually rearmed by compressing the spring from the front end when the injector nose is inserted into a corresponding manual rearming station.

Figure 6A:
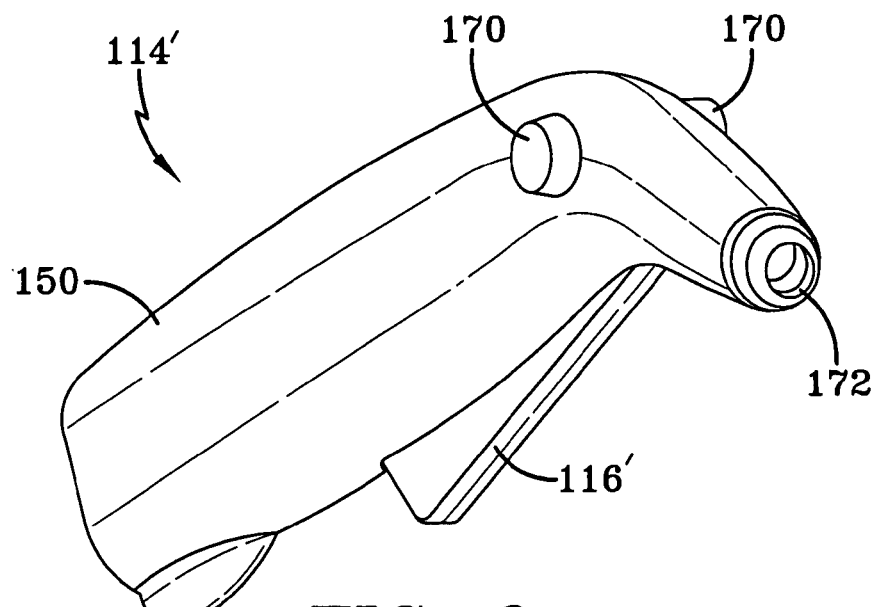
FIG. 6a shows a permanent Motor-In-Tool injector according to the invention, in pictorial form.
Figure 6B:
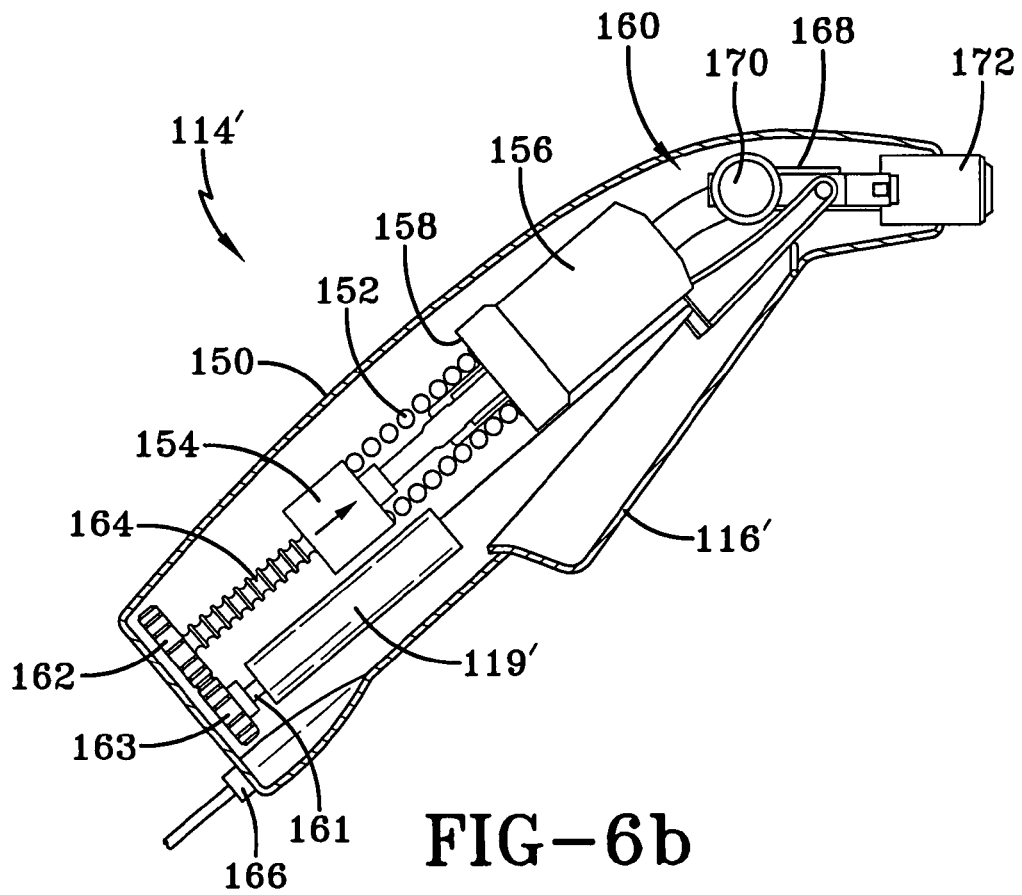
FIG. 6b is a cut-away view of the Motor-In-Tool injector illustrated in FIG. 6a, showing its internal mechanism.

FIGS. 6a and 6b show one version of a complete MIT injector including a handpiece 114', and FIG. 6b is a cut-away view of the motor location and the other significant components. In this case, motor 119' receives power from electrical tether 140 as illustrated in FIG. 5b, but in this case, motor 119' is a permanent fixture on handpiece 114'. This figure also includes an ampule grip/release system, force transfer system, trigger, and the injection spring, all which are also incorporated in the MOT design 100. Ampule 21 is not installed in handpiece 114' in these figures.

With reference to FIG. 6a, handpiece 114' has a housing 150 with a trigger 116'. Turning to FIG. 6b, an injection spring 152 is shown in the compressed state and is held in compression between a ball screw nut 154 and an injection release sleeve 156 having a shoulder 158 against which spring 152 rests, wherein, motor 119' rotates a ball screw 164 which subsequently rotates ball screw nut 154 in the spring compression direction until it reaches and actuates a motor stop switch which is more fully explained with the embodiment of FIG. 7. Optionally, the spring can be made to latch in this position and the motor is instructed to immediately return ball screw nut 154 to a lower portion of ball screw 164. Alternatively, ball screw 154 can stay in the position shown until the injection is given and the used ampule released from the handpiece, at which time, the motor will reverse the ball screw position as described to be reset to again compress spring 152. Both techniques have been implemented, the advantage of immediate reversal is saving time in preparation for the next injection. A force transfer system 160 transfers force from injection spring 152 to system 160 and ultimately to a ram for driving a piston inside an ampule. Motor 119' is mounted in housing 150 and has a drive shaft 161 for rotating a spur gear 163, which in turn rotates a spur gear 162 to rotate ball screw 164 which moves ball screw nut 154 to compress injection spring 152. No thrust bearing is required for protecting drive shaft 161 because the load is decoupled from the motor and the gearbox by virtue of the offset nature of the spur gears. An electric tether connector port 166 is shown as a connection for connecting a battery or, as suggested for the FIG. 5 embodiments, connecting other sources of electrical power to motor 119'.

Force transfer system 160 includes a casing 168 for holding an ampule plunger rod, a transfer mechanism held in casing 168, and a ramrod extending from injection release sleeve 156 to effect the active operation of the transfer mechanism. The ampules are held in handpiece 114' by gripper jaws 172, the operation of which is discussed in further detail for FIG. 8c below. The foregoing mechanism included in handpiece 114', with the exception of motor 119' installed in handpiece 114', is essentially the same as for the MOT handpiece 14.

When trigger 16, 116 or 116' is squeezed on any of handpiece 14, 114, 114', the stored energy in injection spring 152 exerts the appropriate force on transfer system 160 (more fully described below for FIG. 8a), which then applies injection pressure to an ampule ramrod (discussed below). After an injection, an ampule release button 170 is compressed and the ampule capture sleeve (discussed below) is pulled back from its locked position. The gripper jaws 172 expands, are held open, and the used ampule 21 either falls out or is pushed away from the front end of handpiece 114'. There is no need for physical contact by the user; however, if desired, ampule 21 can be inserted and extracted manually. As described above, at some point in the cycle, motor 119' reverses its direction to reset handpiece 114'. To install a new ampule 21, the front end of the handpiece 114' is placed over the mating back section of a new ampule 21, and the capture sleeve is returned to the locked position as soon as gripper jaws 172 are released and closed. The ampule is now securely held in place for the next injection. Apparatus is provided for preventing the actuation of a ramrod for normally injecting injectate from an ampule unless gripper jaws 172 are properly holding an ampule because the actuation of the ramrod without a properly held ampule could pose a dangerous situation since the ramrod could provide a dangerous impact if it were to strike a person.

Figure 7D:
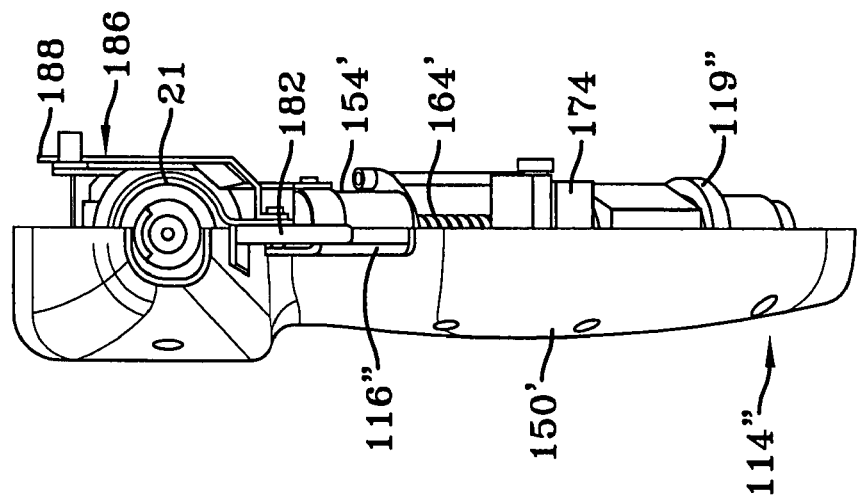
FIG. 7d is a cut-away front view of the injector shown in FIG. 7c showing its internal mechanism in its fired or unarmed condition.

FIGS. 7a, 7b, 7c and 7d show the internal structure for one embodiment of the MIT injector 200. Injector 200 has a handpiece 114" shown in FIGS. 7a and 7b in the armed position, and FIGS. 7c and 7d, the same in the fired or unarmed position. MIT handpiece 114" includes a housing 150' having a ball screw assembly 172, which includes a motor and gear train 119", a coupler mechanism 174, a ball screw 164' and a ball nut 154'. Coupler mechanism 174 represents a fixed point which locks the motor in the housing while at the same time coupling motor 119" and its gear box (included in the motor or housing) to ball screw 164'. Member 174 is able to pivot very slightly (a few degrees) to allow for movement of ball screw 164' and a power linkage 176 as ball screw nut 154' moves up and down on ball screw 164' during the arming process. Coupler mechanism 174 also includes a thrust bearing (not detailed in the figure) to protect the motor and gear train from the in-line spring load. Power linkage 176, described in more detail below, operatively attaches to ball screw assembly 175 with an appropriate connector or pivot point 192. The injector spring is included in a rear or right part of a spring tube assembly 178. A battery 118' is located within housing 150' above spring tube assembly 178. An ampule capture sleeve 180 holds an ampule 21. The discharge or removal of a used ampule 21 is accomplished by the sidewise movement of an ampule release trigger 182. A ready indicator 184 is located at the rear of headpiece 114" and extends out the rear end of injector 200 as shown when the injection spring is compressed. A front view of the unit is shown in FIG. 7b.

Power linkage 176 includes a first link 186 connected to ball screw nut 154' by connector 192 about which first link 186 can pivot. Link 186 has a free end 188 with a longitudinal slot 190. A second link 194 is connected to a pin or pivot pin 196 extending from trigger 116". Second link 194 can pivot about pin 196. A third link 198 is pivotally mounted on a pivot pin 201 carried on a tube housing 202 which allows pivot 201 to slide to the left when the injection spring is released, and a fourth link 204 is mounted at one end to a pivot pin 206 fixed on handpiece 114", and at its other end to a connecting pin 208 extending through slot 190 in first link 186. Link 198 is connected to fourth link 204 by means of the same connecting pin 208 for second link 194. Pin 208 is held in place by a retainer 210.

Figure 7C:
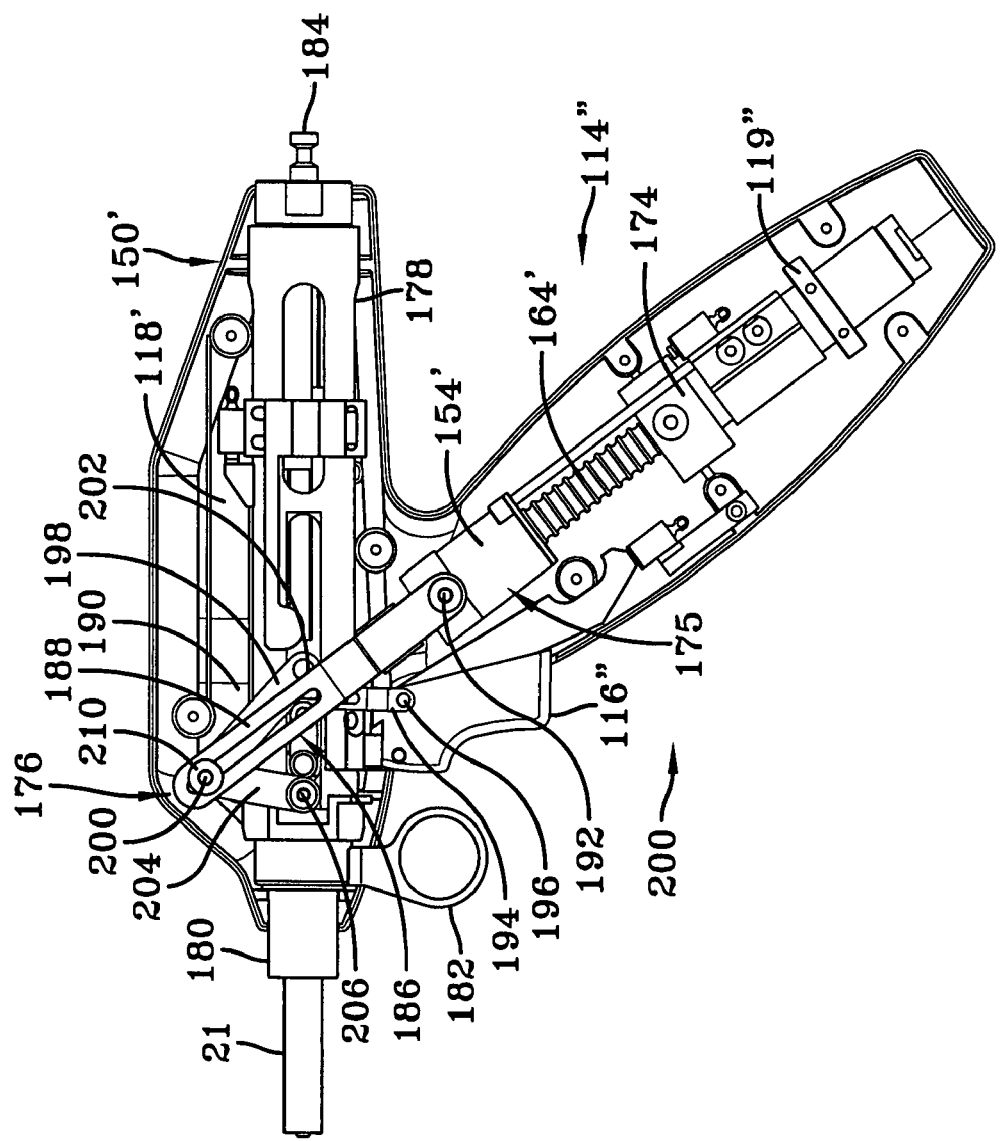
FIG. 7c is a cut-away side view of the injector shown in FIG. 7a showing its internal mechanism in its fired or unarmed condition.

As mentioned, FIG. 7a shows MIT handpiece 114" in a loaded or armed position. When trigger 116" is actuated, injection release or second link 194 is forced upwardly by trigger 116", therein, connecting pin 208 is raised above the center point of links 198 and 204 to unlock these links, and the compression spring in spring tube assembly 178 is released and rapidly moves to the left, driving an ampule plunger rod or ramrod into ampule 21 to cause the discharge of the injectate held therein. Connecting pin 208 moves to the upper end of slot 190 in first link 186, and then, in this embodiment (other motions are possible), upon the sidewise actuation of ampule release trigger 182, an ampule-eject spring engages an ampule ejector sleeve which both withdraws jaw capture sleeve 180 to release jaw expansion springs (not shown in this figure) from holding ampule 21 in place in handpiece 114", and a plunger return and ampule-eject spring drives an ejector sleeve against ampule 21 to either eject or to allow ampule 21 to fall away from the open gripper jaws (discussed in detail with respect to FIG. 8c). The condition of handpiece 114" after firing, i.e. after an injection has been made and just prior to ejection of ampule 21 from the gripping jaws 172, is shown in FIG. 7c.

Ampule release 182 can also release an ampule in the event no injection is made. It also effects release of an ampule if the main system malfunctions.

It is noted that the fully compressed spring in this embodiment latches with a slightly over-center toggle composed of third link 198 and fourth link 204; therefore, spring release is easily facilitated with a small force to the center point of this toggle arrangement when trigger 116" is actuated. Ball nut 154', screw 164' and motor drive 119", move in both the forward and reverse directions by virtue of electrical switch actuation as described below. As described earlier, a ready button 184 extending from the rear end of housing 150' tells the user when injector 114" is fully armed for an injection.

After an injection has been accomplished and injector 200 moves from the condition in FIG. 7a to that of condition 7c, the direction of rotation of the shaft of motor 119" is reversed. Control of motor 119" is facilitated with the use of switches 214, 216, and 218. When trigger 116" is actuated and toggle 204/198 is released to facilitate the injection, trigger 116" also causes a switch arm 212 to move upward with a guide and stop member 220 riding along a slot 213, thereby releasing switch 216. The release of switch 216 enables motor 119", but this alone will not permit it to operate. At this point, there are two possible embodiments for having the motor rearm the injector. In the first embodiment, when ampule release trigger 182 is actuated and the used ampule falls away from the injector, switch 218 is released, and the combination of switch 216 and 218 enable motor 119" to rearm the injector 200, at which time, ball nut 154' moves in the downward direction along screw 164". When nut 154" reaches the bottom of ball screw 164', arm 212 slides downward with guide and stop member 220 riding along slot 213, and switch 216 is again compressed, while at the same time, toggle 204/198 latches to its slightly over center position. Re-compression of switch 216 when ball screw 154' reaches the bottom causes motor 119" to reverse direction and ball 154' immediately returns to the upward part of screw 164 as shown in FIG. 7a. When ball screw 154' reaches the top, it pulls on shaft 215 which in turn produces a slight pull on coupler 174 to pull coupler 174 away from switch 214, and the motor stops. In an alternative embodiment for rearming the injector, motor 119" reversed direction as soon as the injection is completed. This saves time between shots, however, it also provides the risk of dry firing the injector if the trigger is pulled before a new, filled ampule is inserted into the injector. The choice between the two embodiments is determined by the conditions where the injector is to be used.

It should be noted that the manual backup, i.e., for situations where electrical power is unavailable, could be just as fast as automatic arming, but fatigue to the user could be much greater due to the physical energy needed at the rapid rate expected. Whatever the case, the manual feature is necessary to assure that all injections are completed at the location before the healthcare team moves on.

FIGS. 8a-8c illustrate the details of a complete Motor-Off-Tool injector 400; however, the inner workings, with the exception of how it is armed, apply to the Motor-In-Tool injector as well.

The FIG. 8a cut-away shows the off-axis energy transfer system consisting of a series of balls in a tube and all of the other elements described above. The off-axis transfer of power was developed in order to provide a handpiece that was less threatening to children than the gun type structure that has typically been used. This model is also easier to handle than the straight-line version (similar in shape to a conventional flashlight), provides for a better distribution of weight, and helps reduce the onset of fatigue to the healthcare worker. Several methods were reduced to practice, each having its own advantages and disadvantages for certain situations in mass immunization.

Referring to FIG. 8a, MOT 400 includes a handpiece 414 having a housing 450 with a trigger 416, and a force transfer system 402 having ampule plunger rod 403, force transfer balls 405 and a ramrod 407. Force transfer balls 405 are held in and tangential to the inside surface of curved housing 409. Handpiece 414 further includes a draw rod 411, a spring tube 413 housing an injection spring 415 and a spring retainer nut 417. An injection release sleeve 456 includes part of curved housing 409 with force transfer balls 405, as well as six release balls 419 which can be transferred from an annular channel 421 to an annular pocket 423. Handpiece 414 has an ampule release button 425 and leaf springs 427. Ampule release from the front end jaw structure is essentially the same as that described for FIG. 8c below.

FIG. 8b is a blown-up view of force transfer balls 405 shown in FIG. 5a. Balls 405 are preferably made from steel, and there are "hat" members 429 inserted between each of the balls that are intended to improve the efficiency of this transfer by helping maintain alignment of the balls to reduce wall friction. Hat members 429 are preferably made from Delrin. While not shown in the figures, tube 409 can also contain a hydraulic fluid with sealing pistons at either end, rather than balls 405. The fluid, along with these pistons, will transfer the power to ampule plunger rod 403 when the injection spring 415 is released. Tubular transfer system 402 is the most compact and lightest weight of those disclosed; however, its efficiency is not as great as some of the others; for example, while somewhat larger, a chain or cable connected to a pulley and gear motor combination can also provide the spring compression at higher efficiency. Selection of a particular transfer system will depend on the energy available to accommodate an acceptable efficiency, as well as the premium placed on weight and size of the device.

FIG. 8c is a blown up view of the circular jaw structure shown in FIG. 8a. As pointed out earlier and discussed below, these jaws allow for a no-personal contact procedure when grasping and discarding an ampule, and because of that, they also have important utility for personal use injectors when used by healthcare workers for a particular patient who might be harboring dangerous blood born pathogens, thus eliminating the risk of cross infection to the worker.

In FIG. 8c, an ampule 21 is held in handpiece 414 by three gripper jaws 472. Ampule 21 has a housing 700 with a cylindrical forward outer surface 702 and a tapered rearward surface 704 that is narrow at its free end and thickens until it reaches a peak 706 after which it tapers inwardly towards the longitudinal axis of ampule 21 to form a slanting shoulder 708. Gripper jaws 472 each have a head 475 with an inclined ampule engaging surface 476 for engaging ampule shoulder 708. Jaws 472 are biased outwardly by jaw expansion springs 478. A jaw capture sleeve 480 engages an abutment 482 on the outside of head 475 of jaws 472 to hold jaws 472 in a closed position against the bias of springs 478. Plunger rod 403 follows the longitudinal axis of jaws 472 and ampule 21 (if installed), and as explained earlier, effects the ejection of serum or other injectate from ampule 21. A guide and holder 484 has a forward end portion with an inclined inner surface 486 for engaging and holding inclined rearward surface 704 of ampule 21, an inward collar 488 and a rearward cylindrical portion 490. An ejector sleeve 492 extends partially along plunger rod 403, and the inner surface of collar 488 of rearward portion 490 of gripper jaws 472 engages sleeve 492 and holds it against plunger rod 403. A plunger return and ampule spring 494 extends partially along plunger rod 403, including a forward portion between ejector sleeve 492 and plunger rod 403.

A jaw capture sleeve return spring 496 extends along the inside surface of the rear part 497 of jaw capture sleeve 480, and has a forward end abutting an inwardly extending collar 498 of sleeve 480 and a rear end abutting a gasket 500 extending between the rearward end of sleeve 480 and the rearward portion 490 of guide and holder 484. A retaining ring 502 is located in an annular groove 504 of guide and holder 484 for maintaining gasket 500 and sleeve and return spring 496 in place.

FIG. 8a shows the MOT injector 400 in its loaded or armed condition, ready for giving an injection. The user actuates trigger 416 by causing it to pivot on an annular axle (hidden in this figure but located close to the left end centerline of plunger rod 403), which causes a cam 506 on trigger 416 to engage an inclined surface 508 to force injection release sleeve 456 downwardly along tube 409 containing balls 405. This causes injection release balls 419 to move from annular channel 421 into annular pocket 423 in injection release sleeve 456. Balls 419, which had been restricting the release of injection spring 415 in spring tube 413, now permit the release of spring 415. Therein, injection spring 415, which at its upper end engages a drive member 510, in turn drives draw rod 411 into ramrod 407 to apply the force from spring 415 into force transfer balls 405 to move upwardly, the forward ones of which moving around the curve in the upper end of tube 409, to drive plunger rod 403 into the inner end of ampule 21 of such force as to cause the ejection of injectate under jet pressure through its discharge port 710.

It is noted that ampule 21 in this embodiment is shown with an exit port perforator 460 covered by a collapsible protective front end 462 whose interior contains a springy or resilient return material. When front end 462 is pressed against an injection site, it collapses under the applied force to then expose perforator 460 through the narrow access hole at the front. The perforator now enters the very outer layer of the body and the injection is thereafter delivered. When the injection is completed, protective cover 462 re-expands to again cover perforator 460 thus avoiding the risk of injury to the user. Importantly, protective front end 462 is manufactured with a side-wise bias that breaks lose when the perforator is first exposed, consequently, when perforator 460 is drawn back into protective front end 462, the narrow exit hole in 462 will shift to the side as shown in FIG. 8d, therefore making it impossible to again expose perforator 460. This feature provides protection against any form of after shot "stick" or reuse by preventing the perforator from again becoming exposed, and will, in fact, destroy the perforator is such front end compression is again applied.

Thereafter, the actuation of ampule release button 425 withdraws jaw capture sleeve 480 to the left as shown in FIG. 8c, away from forward end 702 of ampule 21. This results in jaw expansion springs 478 rotating gripper jaws away from ampule 21 so that ampule-engaging surface 476 disengages ampule shoulder 708. Plunger return and ampule-eject spring 494 urges ejection sleeve 492 forwardly against the rear face 712 of ampule 21 to eject ampule 21 from MOT handpiece 414.

Since this embodiment is that of a motor-off-tool (MOT) injector, withdrawal of ramrod 407 from the forward or fired position must first be facilitated before a new ampule can be inserted into gripper jaws 472. Thus, injector 414 is inserted into either a motor driven arming station or a manually driven arming station to grab hold of draw rod 411 and pull on it to recompress spring 415 to the injection ready position. A new ampule 21 can now be inserted in the forward end 485 of guide and holder 484, and jaw heads 475 will ride along inclined surface 704 of ampule 21 until peak 706 rides over the gripping portion of jaw head 475 to releasably lock ampule 21 in place. Jaw capture sleeve return spring 496 then moves jaw capture sleeve 480 to the right as shown in FIG. 8c, to move gripper jaws 472 to the closed position.

MOT handpiece 414 is now ready for the next injection. The entire system in this and other embodiments have been found to make 600 injections per hour, including the injection of injectate from each ampule, discarding the ampule and reloading a new ampule.

Figure 9:
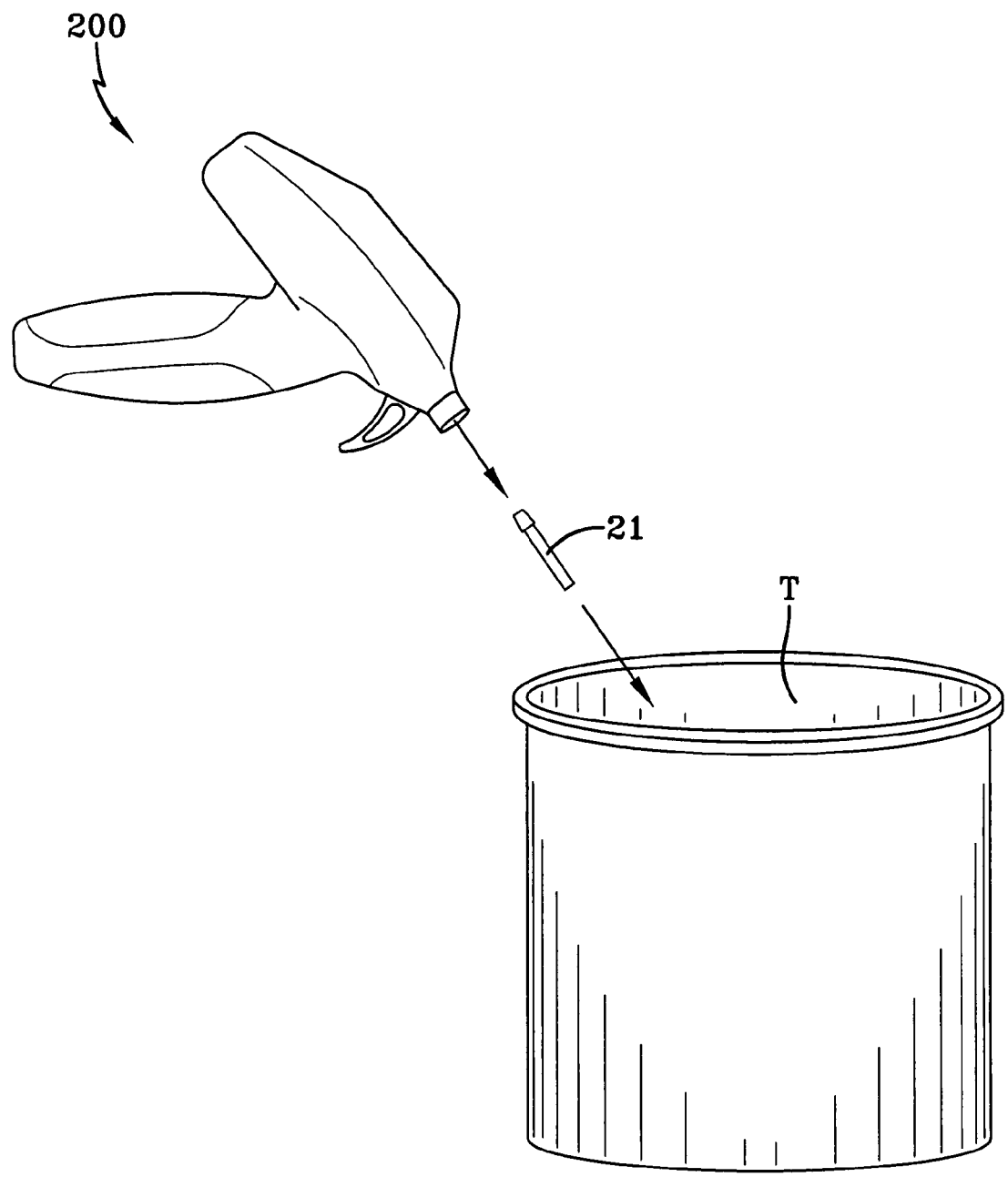
FIG. 9 is a pictorial view of a used ampule being ejected from the jaw structure shown in FIG. 8c.

FIG. 9 illustrates a full external view of the FIG. 7a-7c MIT injector 200 as seen when ejecting a used ampule 21 into a trash container T without the need for any physical contact by the user.

Figure 10A:
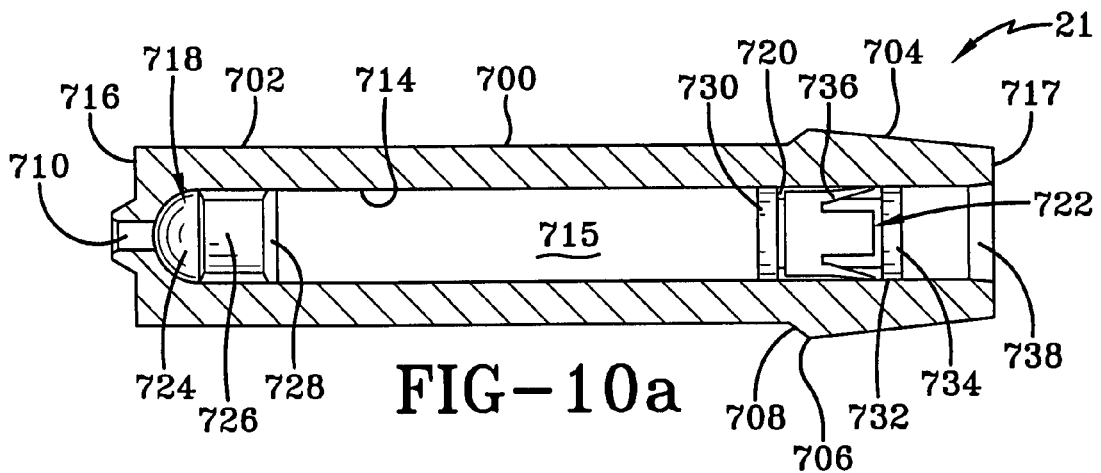
FIG. 10a is a pictorial view of an unused, empty ampule according to an embodiment of the invention.
Figure 10B:
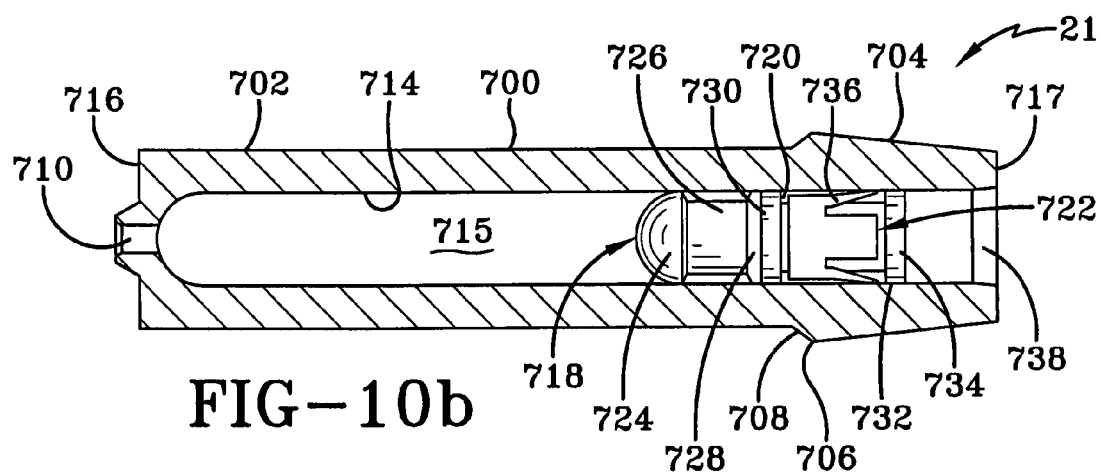
FIG. 10b is a pictorial view of the ampule shown in FIG. 10a filled and ready to deliver an injection.
Figure 10C:
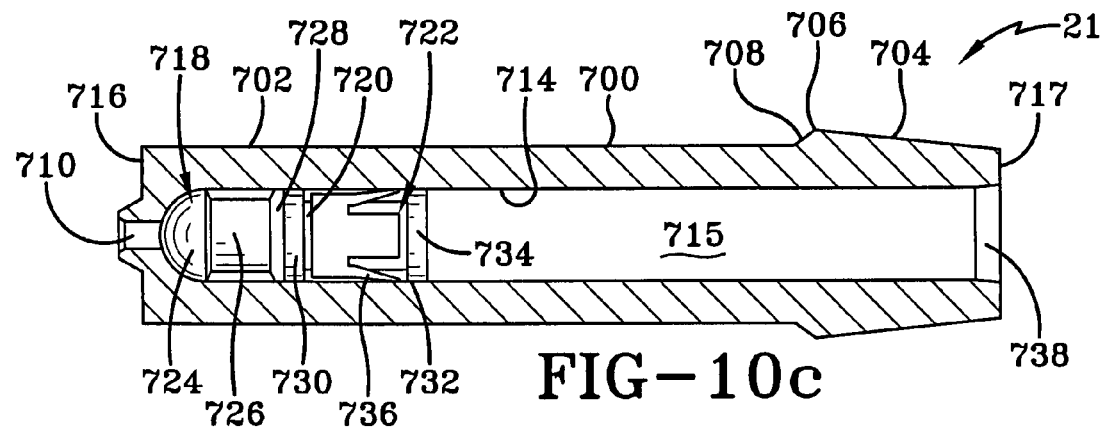
FIG. 10c is a pictorial view of the ampule shown in FIG. 10a in the disabled state after an injection has been given.

FIGS. 10a-10c are three views of one version of a self-destruct ampule that is conveniently used with this injection system.

FIG. 10a shows ampule 21 prior to filling. In order to maintain consistency as to the location of the proximal and distal ends of the ampule for the discussions to follow, the proximal end is always that end which is closest to the injector, i.e., the part of the ampule that is held by the grasping jaws described earlier. Each ampule 21 includes its thin plastic shell or housing 700, cylindrical forward outer surface 702, tapered rearward surface 704, peak 706, shoulder 708, an orifice or discharge port 710 and rear face or proximal end 717. A channel or bore 714 forms a chamber 715 extending along the longitudinal axis of ampule 21, and is open at the rearward or proximal end 717 of ampule 21. Orifice 710 is located at the forward or distal end 716. Injection piston 718 is located at the distal end 716 while a spool 720 and a locking spring assembly 722 remain at proximal end 717. Piston 718 is made from an appropriate plastic and has a head portion 724, a body 726 and a base 728. Spool 720 has a head 730, a body 732 and a base 734. Locking spring 722 is wrapped around body 732 of spool 720, and has leaf spring members or fingers 736 which are biased outwardly from the longitudinal axis of ampule 21 towards the side wall 714 of chamber 715. The leaf members 736 of the locking spring 722 apply slight outward pressure to the inner diameter (ID) of bore 714, thus enabling locking spring assembly 722 to maintain position within bore 714. Herein lies another feature that, in some cases, would find use with a personal use injector. However, it should be noted that in some cases where dangerous pathogens are not an issue, some personal use injectors actually promote the reuse of ampules to facilitate greater economy to the user.

FIG. 10b shows a filled ampule. The distal end 716 of ampule 21 is installed into the filling station (shown in greater detail in FIG. 19), and pressurized injectate is forced into chamber 714 through the orifice 710, thus driving piston 718 towards spool assembly 720 at proximal end 717 of ampule 21, wherein it makes physical contact with spool 720 and locking spring 722 and comes to a stop. Due to outward pointing fingers 736 of locking spring 722, assembly 720 is unable to move any further in the proximal direction. The concept of filling through the exit port with the application of pressure to the vaccine reservoir offers a substantial advantage by avoiding the insertion of air into the injectate chamber during the filling process. This as opposed to the more common practice of creating a vacuum in the injectate chamber when the plunger is pulled back. While the pulling procedure certainly draws fluid into the injectate chamber, it also draws air in at the same time, therein requiring an extra step of carefully pushing the plunger forward until all of the air is expelled before giving the shot.

FIG. 10c depicts an ampule 21 after the injection is completed. Plunger rod 403 makes contact with end or base 734 of spool 720, thus driving the spool 720, locking spring assembly 722 and piston 718 forward at high speed to force the high velocity injectate out through orifice 710 as a coherent jet stream. Once the injection is complete, piston 718 is firmly lodged in distal end 716 of ampule 21, making reuse virtually impossible to further reduce the likelihood of cross infection.

FIGS. 11a-11c depict an alternate embodiment of the piston used in ampule 21 that avoids the use of a locking spring to disable the ampule, but relies instead on a very thin frangible section just behind an O-ring seal on the piston. After the piston reaches the end of the injection stroke and strikes the distal end of the ampule, the injector ram continues in the forward direction just far enough to produce an additional compression force on the piston which provokes a separation, or breakage, of the piston at the frangible ring. Once the piston is broken into two parts, reuse of the ampule is impossible. In another form of the same idea, the injector ram fractures a frangible center section on the piston. After the piston has fully pushed forward to complete the shot, a movable center rod will continue beyond the end of the ram and force a hole in the frangible member; therefore, if a user tries to refill the ampule, the remains of the piston cannot be moved to the full position.

Thus, still referring to FIGS. 11a and 11b, an ampule piston 750 is shown. Piston 750 has a head 752, a body 753, and an annular groove 754 separated by a pair of surfaces 756, 758 by a distance sufficient to engage in sealing contact an O-ring 760. An elongated, annular groove 762 extends between a pair of collars 764, 766. A closed bore 768 (FIG. 11c) extends from an end 770 of piston 750 and ends in a conical surface 772. The narrow portion 774 between conical surface 772 and surface 758 of groove 754 forms a frangible web area. As explained above, in use a ram such as ampule plunger rod 403—when activated—is driven into the rear surface 770 of piston 750 as it moves through its injection stroke to eject injectate from an ampule such as ampule 21 from chamber 715 through orifice 710. After ampule piston 750 reaches the bottom of ampule 21, plunger rod 403 continues its forward motion until its compressive force breaks the frangible web area at narrow portion 774, rendering piston 750 useless and ampule 21 disabled against reuse.

Figure 12A:
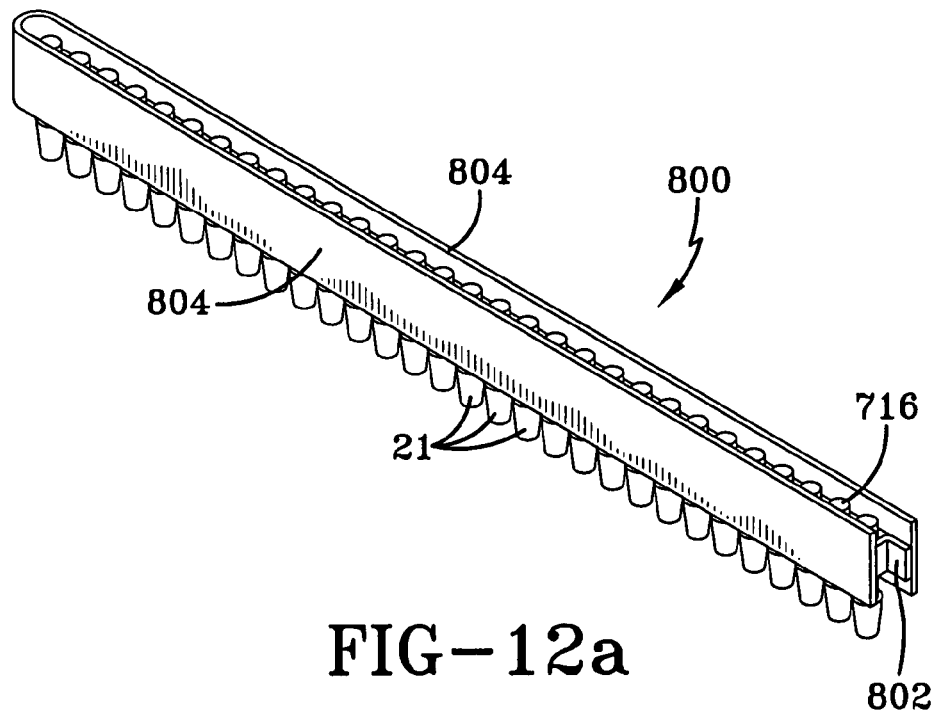
FIG. 12a is a pictorial view of a portion of the invention showing ampules attached to a cardboard/paper strip.
Figure 12B:
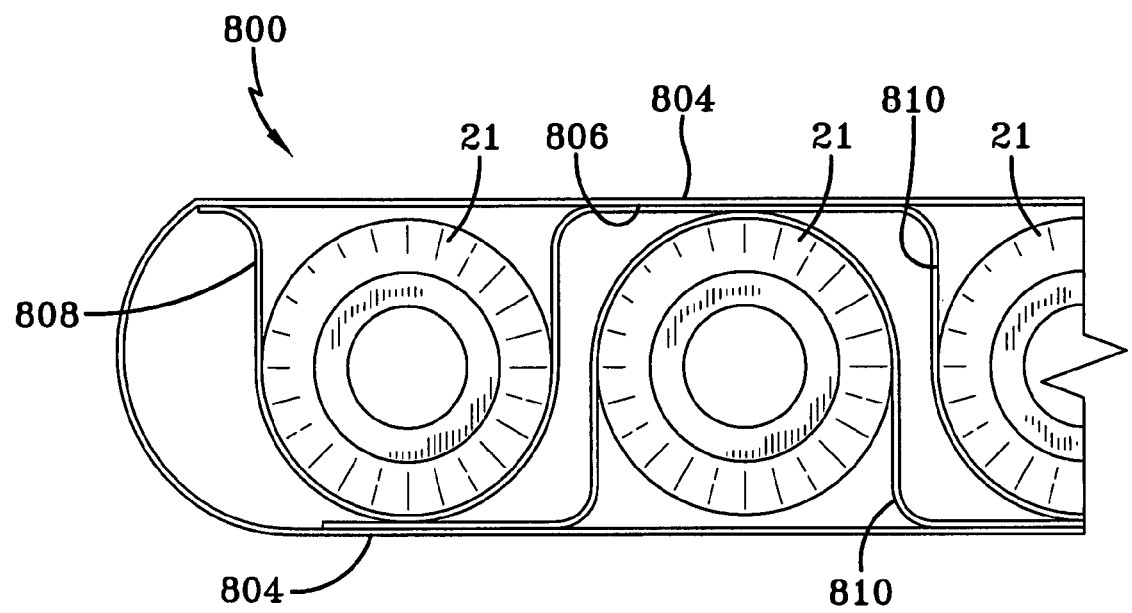

The item shown in FIGS. 12a and 12b is an example of ampules 21 connected together on an ampule strip 800 comprising a cardboard and paper combination, with tear-away paper strip 802 looping over each of the ampules as they rest on cardboard backing 804. Ampules 21 are affixed to the cardboard backing when the paper overlay 802 is secured to the cardboard backing 804 by a suitable adhesive 806. Cardboard backing 804 extends beyond distal face 716 of each ampule 21, protecting the orifice 710 from incidental contact and possible contamination during handling. A loop belt 808 is configured and serpentined in such a way as to form folds 810 to hold ampules 21 securely inside of each other in the folded over strip during shipping, handling, and filling, but allows ampules 21 to be easily torn away when a shear load is applied by the handpiece jaws (such as jaws 472) when pulling ampules 21 out of ampule strip 800, i.e., a tear-away system. Ampules 21 in FIGS. 12a and 12b are shown prior to insertion into the magazine system (described in more detail below). An alternate embodiment (not shown) has the ampules connected together during the molding process, but insertion into the magazine and the tear, or breakaway feature is essentially the same.

Each ampule strip 800 preferably contains a number of 0.5 ml ampules 21. Reconstitution of a 50-dose cake of lyophilized vaccine with 30 ml of diluent typically yields more than 50 doses of vaccine, especially with the highly efficient filling station described below. While a greater number is possible, the number of ampules in the strip will be equal to half the average number of doses of vaccine the filling station will extract from the vial (i.e. two ampule strips per vial of vaccine, wherein a strip will preferably hold between 26-28 ampules). As shown in FIGS. 12a and 12b, ampules 21 are spaced approximately 10 mm (0.400") apart, allowing strip 800 to fold in half lengthwise (FIG. 12a), nesting ampules 21 facing one another into the intervening spaces (FIG. 12b) for ease of shipping and filling.

The folded strip will be removed from its sterile pouch and interfaced directly with the filling station (as discussed below) advancing iteratively to allow the filling nozzle to access each ampule 21 and force reconstituted vaccine through its orifice 710 described above for FIGS. 10a-10c. The vaccine will push ampule piston (such as piston 718 or 750) back until it stops against a pre-installed spool (such as spool 720) and lock ring (such as locking ring 722), insuring a precise amount of injectate in each ampule 21. This spool and lock ring will also prevent the piston from moving in the reverse direction once the injection is completed, thus disabling the ampule and preventing reuse. Once the ampules 21 are filled, strip 800 is ready to go into cold storage for use later in the day or to be installed directly into a magazine.

FIGS. 13a-13d and 14a-14b show two distinct, yet similar, off-tool ampule management systems available with the injection station of FIG. 1, and the handpiece designs described above. By virtue of the ampule strip design in FIGS. 12a-12b, a greater number of ampules are available for the off-tool magazines than that described for the on-tool magazines of prior art patent U.S. Pat. No. 5,318,522. Either of the magazines can be attached to a working surface, such as the injection system carry case, a table, a lanyard around the user's neck, belt pack, arm pack or wrist mounting, and/or any other convenient location.

Figure 13A:
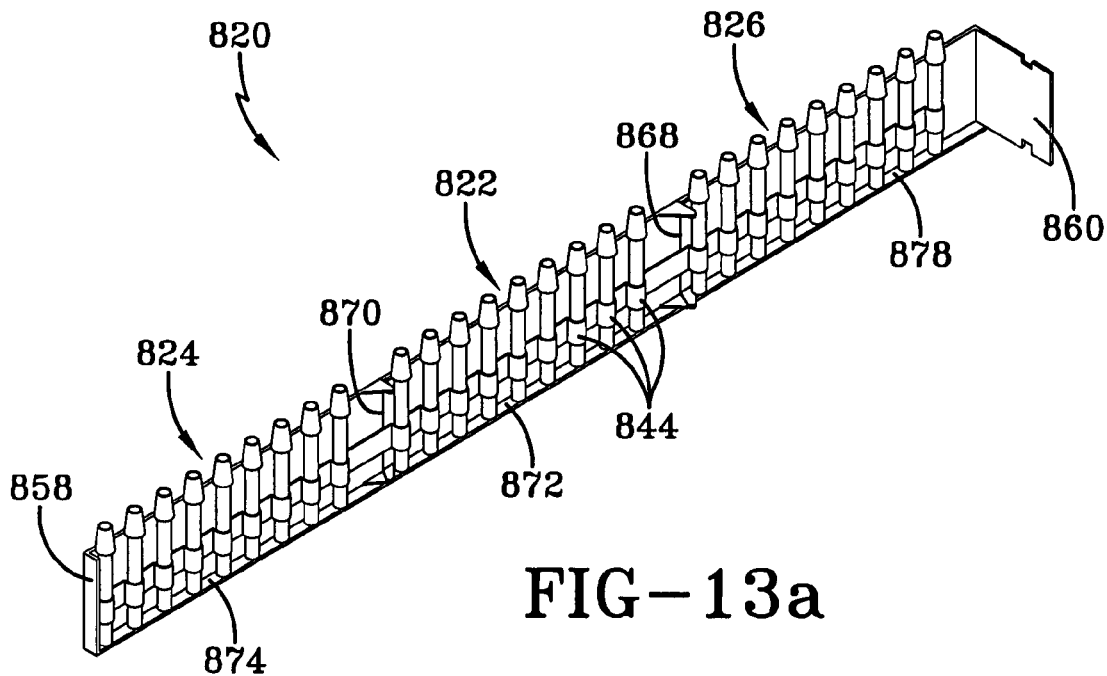
FIG. 13a is a pictorial view of the ampule strip shown in FIG. 12a when inserted in an unfolded magazine.
Figure 13B:
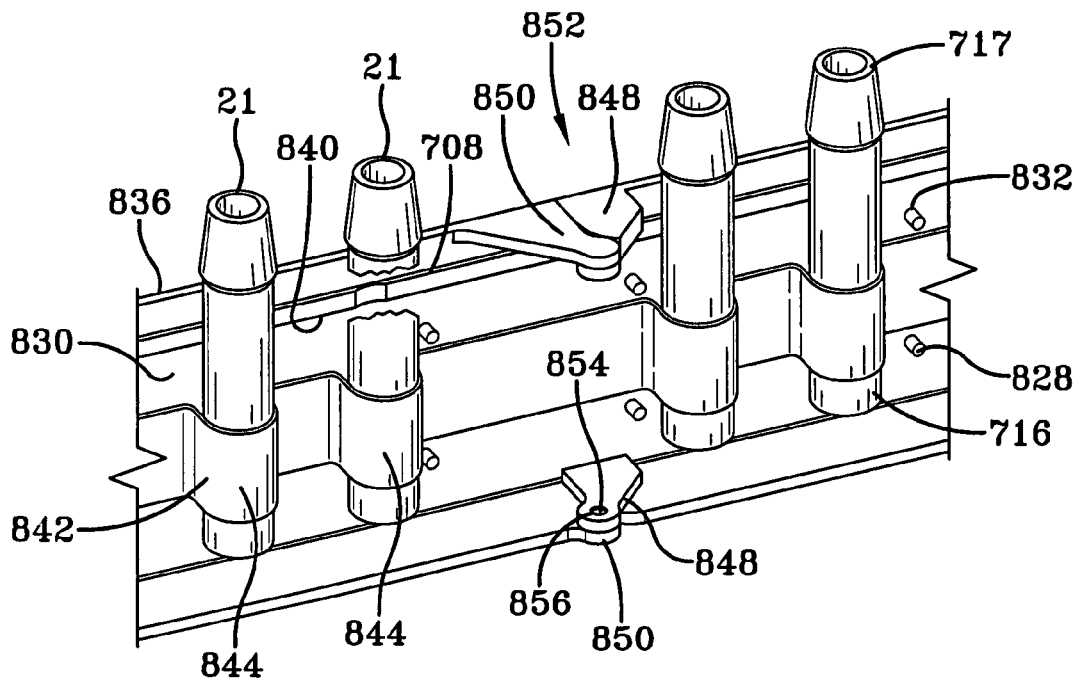
FIG. 13b is an enlargement of a portion of FIG. 13a showing a close-up view of posts for securing ampule strips to a folding magazine.
Figure 13C:
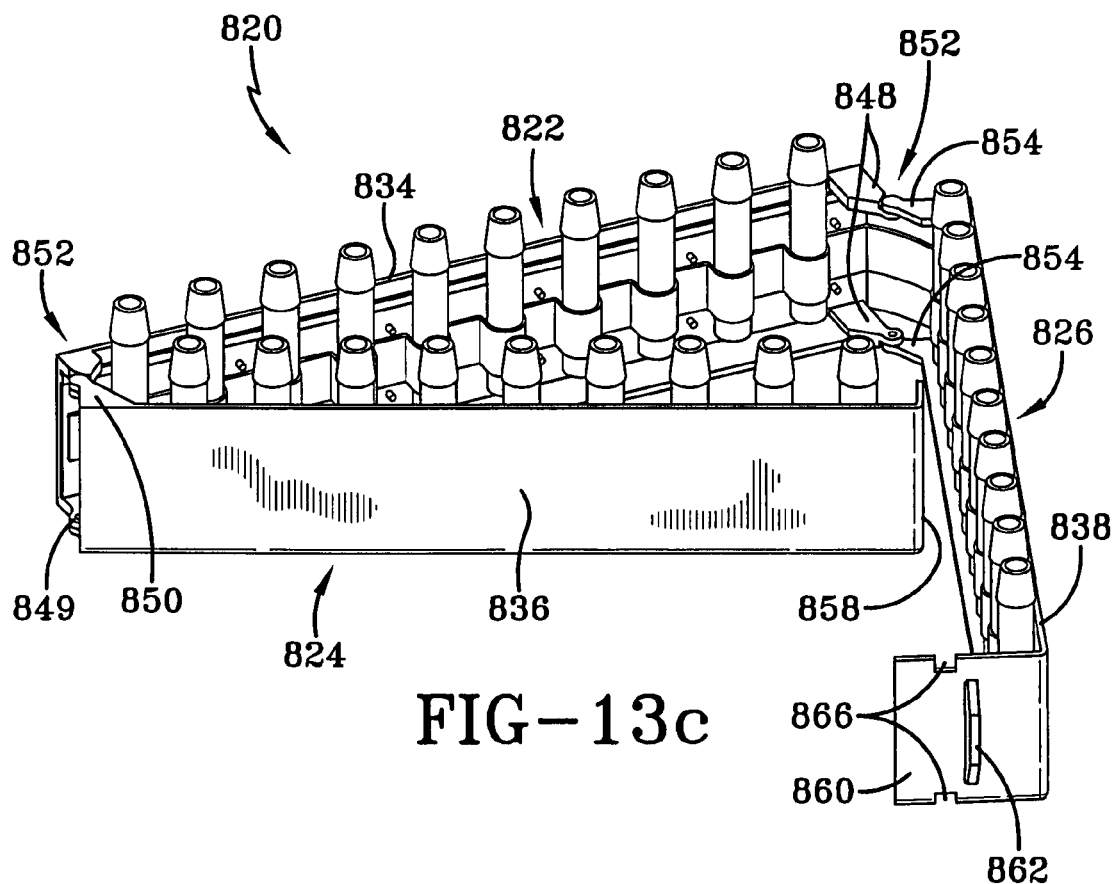
FIG. 13c is a pictorial view of the apparatus shown in FIG. 13a with a set of magazine wings being folded over the center segment.
Figure 13D:
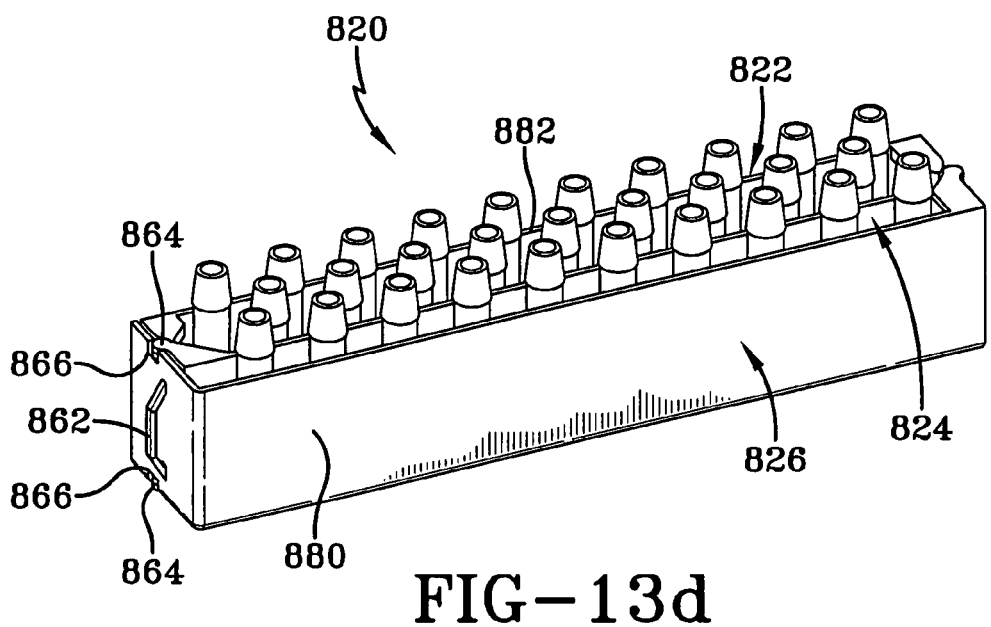
FIG. 13d is a pictorial view of the apparatus of FIG. 13a in a fully-folded magazine ready for injection.

The magazine 820 shown in FIGS. 13a-13b is a folding magazine. This system holds a set of ampules 21 in a fixed position relative to one another, and are removed from any location, one at a time by the handpiece. This system comprises three plastic segments: a center segment 822 and two winged sections 824, 826 hinged to each side. Segments 822, 824, 826 are initially unfolded, and the open magazine is placed on a flat surface, allowing the ampule strip to be laid into the unfolded magazine (FIG. 13a). Small posts 828 (FIG. 13b) on the inner surface of magazine segments 822, 824, 826 press securely into a set of matching holes 832 in an ampule strip backing 830, properly locating strip backing 830 on the support walls 834, 836, 838 (FIG. 13c) on each of segments 822, 824, 826, and holding it in place. Additionally, an edge 840 of backing 830 closest to proximal end 717 of ampules 21 fits firmly against retaining rib 708 on the inside surface of magazine segments 822, 824, 826, keeping strip backing 830 from sliding while ampules 21 are being extracted one at a time. Ampule strip 800 when inserted in magazine 820 includes a loop belt 842 attached to strip backing 830 by an appropriate means such as an adhesive. Loop belt 842 and backing 830 are flexible so that they can bend with the folding of magazine 820. Loop belt 842 has a sequence of loops 844 being generally semi-cylindrical for grasping ampules 21 around ampule body 702 to hold ampules 21 in place. Retaining rib 708 extends across each of segments 822, 824, 826 for engaging the edge of ampule strip 800 when it is inserted in the magazine. Segment 822 has two pairs of opposing hinge arms 848, 849 for cooperating with hinge arms 850 on each of segments 824, 826 for forming two pairs of hinges 852. Hinge arms 850 each have a pin 854 for extending through a hole 856 in hinge arms 848, 849 to complete respective hinges 852. Segment 824 has an end plate 858 and segment 826 has an end plate 860 with a handle 862 attached to it by some appropriate means or to be integral therewith. Finally, the segments 824, 826 are folded over center segment 822, left segment 824 first (FIG. 13c). The end of right segment 826 snaps fully over the opposite ends of the center segment 822 and left segment 824, holding the system securely closed in its folded position (FIG. 13d). Snapping occurs by virtue of opposing fingers 864 extending from hinge arms 850 into opposing notches 866 in end plate 860. Strip backing 830 and loop belt 842 have strategically positioned pleats or perforations 868, 870 to allow the folding to occur easily. The folded magazine 820 (FIG. 13d) has a solid bottom surface because of foot flanges 872, 874, 878 on each of segments 822, 824, 826, to protect ampule distal ends 716 and also to provide a place for possibly securing magazine 820 to a surface, either through hook-and-loop strips (e.g. Velcro©) or features which affix to matching surfaces on the injection system carry case. Folded magazine 820 also has solid sides 880, 882, which allow for gripping the magazine with one hand while extracting the ampules with the handpiece jaws. The relative position of the ampules in the magazine allows access to each ampule in turn. Proximal ends 717 of the remaining ampules provide some guidance to the nose of the handpiece, helping the user locate the handpiece nose (such as gripper jaw heads 475) appropriately for jaws (such as jaws 472) to grasp the targeted ampule. After the last ampule 21 has been extracted, magazine 820 can be unfolded, ampule strip backing 830 removed and discarded, and a new strip backing 830 of filled ampules 21 installed. The advantage of folding magazine 820 is simplicity. With few parts and few manipulations necessary to operate, this magazine design is likely to be robust and take minimal time to load and unload. Protection of the orifice or distal end 716 of ampule 21 prevents the possibility of cross infection, but because proximal ends 717 of ampules 21 are exposed, some effort must be made by the user to insure cleanliness.

Figure 14A:
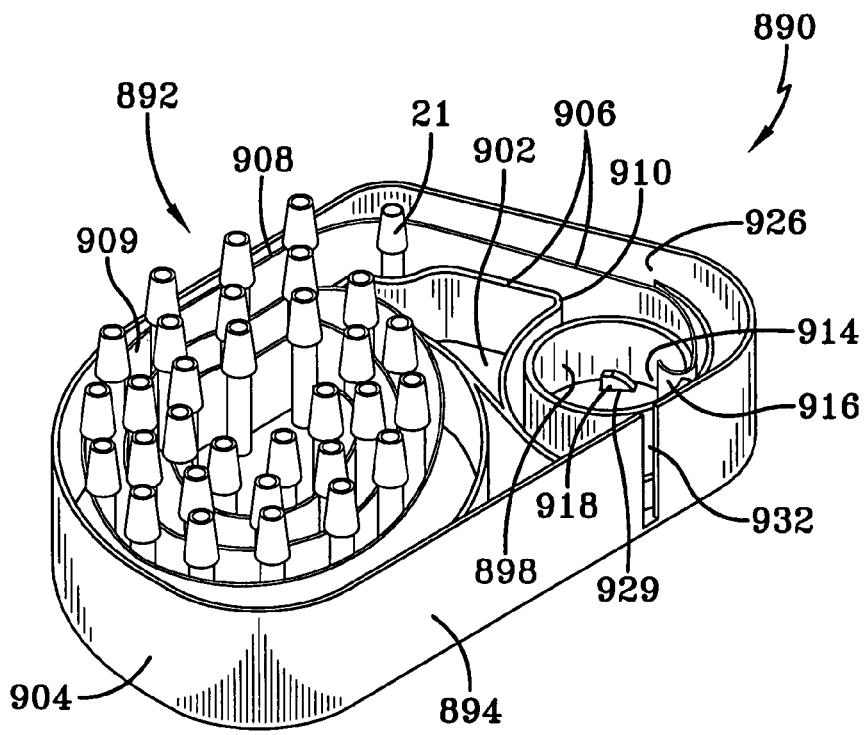
FIG. 14a is a pictorial view of another embodiment of an aspect of the invention showing an ampule strip coiled up and placed in a rotating auto-feed magazine.
Figure 14B:
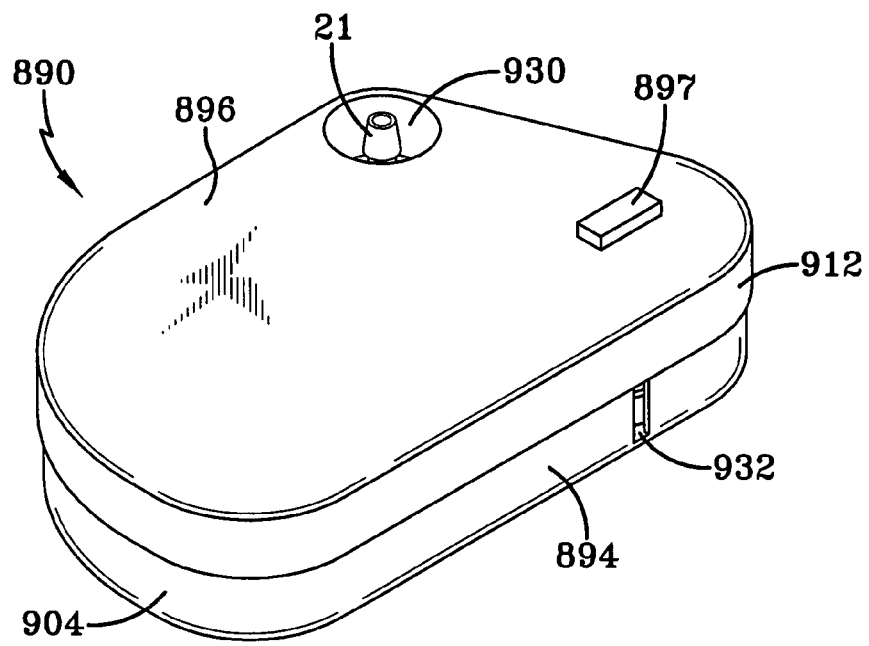
FIG. 14b is a pictorial view of the embodiment shown in FIG. 14a with a cover placed on the rotating auto-feed magazine shown in FIG. 14a and ready for use.
Figure 14C:
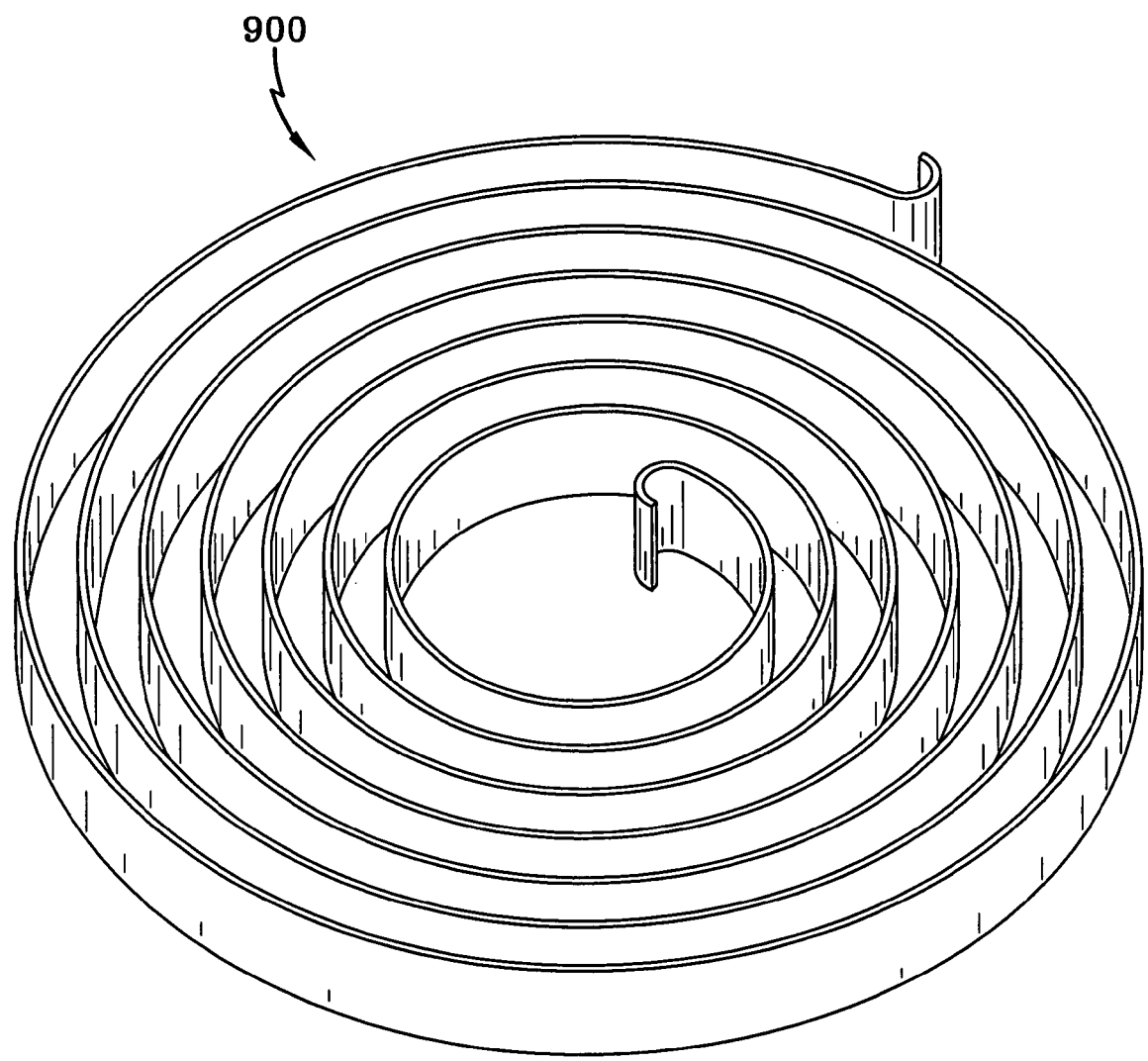
FIG. 14c is a pictorial view of a negator spring used in the magazine shown in FIGS. 14a-14b, 16, 17 and 18a-18c.

FIGS. 14a-14b illustrate a rotating auto-feed magazine 890. This system advances the ampule strip along a track, presenting each ampule at a consistent location for extraction. As with folding magazine 820, this system 890 is ideal for placement on a table, attached to the injection system case, or ideally, on the opposite wrist to the hand used to hold the injector. If desired, auto-feed magazine 890 could also be worn as a neck lanyard by the vaccinator. This magazine 890 comprises a load chamber 892 that holds the ampule strip (such as strip 800 of FIG. 12a) and a rotating take-up spool 898 that collects the empty strip as the ampules are removed, and is similar in operation to the film advance system of a camera (FIG. 14a). This embodiment includes four primary components: a base 894, a cover 896 (FIG. 14b), take-up spool 898, and a constant-force negator spring 900 (FIG. 14c) located and attached to the inside of spool 898. Spring 900 is shown outside of spool 898 with FIG. 14c for clarity. Housing base 894 has a bottom wall 902, side walls 904 and interior guide walls 906 for cooperating with the inside surfaces of side walls 904 to guide strip backing 908 of ampule strips 909 through load chamber 892. Wall 906 is also appropriately curved at wall section 910 so that load chamber 892 can receive take-up spool 898. Cover 896 has a rim 912 that is configured to slip over and slidingly engage the upper portion of side walls 904. Take-up spool 898 has a slot 914 for receiving a tab 916 and strip backing 908, for holding tab 916 as take-up spool 898 rotates to draw ampule strip 800 (or 900 in FIG. 14a) along its path in magazine 890. Ampule strip 909 has ampules 21 secured to strip backing 908 by some appropriate means, such as disclosed with reference to FIGS. 13a-13d.

Figure 14D:
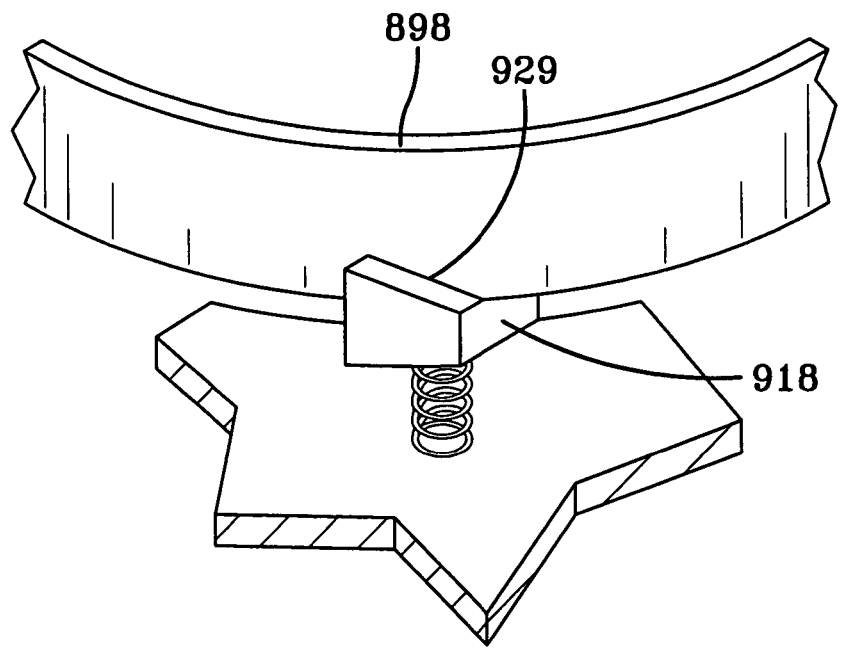
FIGS. 14d and 14e are schematic drawings of a pawl and ratchet device used in the magazine shown in FIGS. 14a, 14b, 16, 17 and 18a-18c.
Figure 14E:
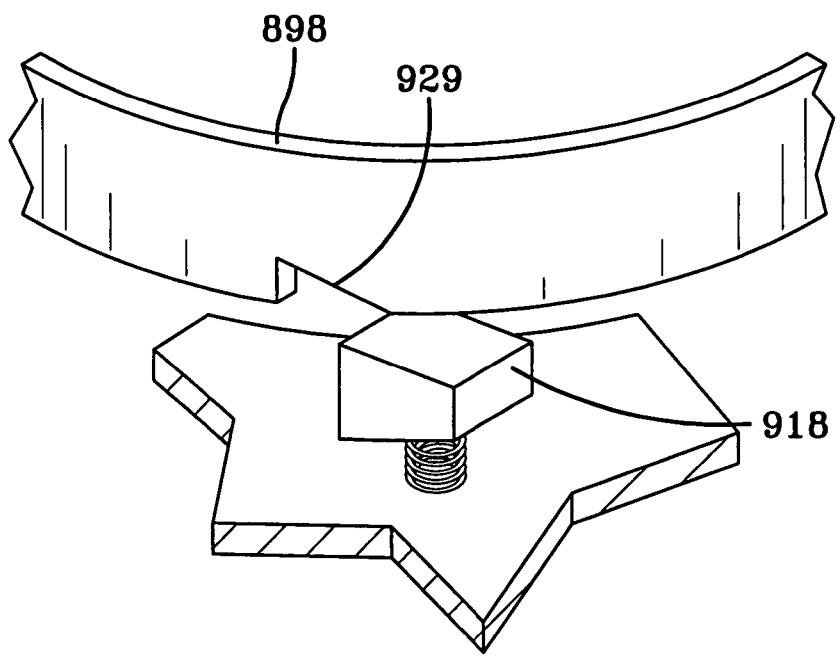

In preparation for inserting ampule strip 909 into magazine 890, the user pulls the wind-up cord (not shown, but see FIG. 17 for an equivalent one) which turns take-up spool 898 through several revolutions (counterclockwise in this figure) to turn spring 900 to the fully wound and latched position. A ratchet-type arrangement having a pawl 918 and a ratchet groove 929 will prevent the cord from being pulled back into the housing by wound up spring 900 because of the vertical left side on groove 929 and mating spring loaded pawl 918 on the interior of magazine 890, however, the slanted surface on the right side of groove 929 will allow spool 898 to rotate in the counter clockwise direction during wind-up by having spring loaded member 918 slide over the slanted surface during each revolution. To facilitate loading magazine 890, ampule strip 800 is rolled into a coil and placed in load chamber 892 (FIG. 14*a*). The user then threads an extended tail or tab 916 of strip backing 908 along the track or path as described above, affixing it to rotatable take-up spool 898. When cover 896 is placed on to housing base 894, an appendage on the inside of cover 896 (not shown) extends downward to interface with the surface of spring loaded pawl 918 and push it out of the way to release take up spool 898. Application of spring tension from constant force spring 900 located in housing base 894 draws strip backing 908 onto spool 898 until an ampule 21 comes to rest against a stop position defined by wall portion 926. Cover 896, which can optionally be attached to the housing base by a hinge on housing base 894, is then placed over base 894 to protect the ampules against contamination (FIG. 14*b*). As stated above, the ratchet is released when pawl 918 is pushed out of mating groove 929 in the closing of cover 896. This should be made clear by considering FIGS. 14*d* and 14*e*. In order to cock or set spring 900 prior to the loading of a strip of ampules, a pull cord is pulled to rotate spool 898 counterclockwise. As spool 898 is wound counterclockwise as shown in FIG. 14*a*, spring loaded pawl 918 slides into groove 929 but does not stop the rotation due to the sliding of the inclined surfaces of pawl 918 and groove 929 passing over each other. However, once a strip of ampules is inserted in load chamber 892, spring 890 would be free to unwind spool 898. This cannot occur, however, since while spring 900 could unwind, spool 898 moves a small amount due to pawl 918 moving below spool 898 as shown in FIG. 14*e*. Nevertheless, while pawl 918 moves into groove 929 as shown in FIG. 14*d*, the ampule strip is locked in place. When cover 896 is closed, a bar 897 moves pawl 918 downward so that it cannot stop the clockwise rotation of spool 898 as ampules are advanced through magazine 890. This action-reaction will free spring 900 and advance ampules 21 on backing strip 908 as described.

A funnel-like opening 930 in cover 896 provides access to the ampule 21 resting against the stop defined by wall portion 926. The funnel feature allows the nose (the head of the gripping jaws) of the handpiece to be guided easily into position to grasp the ampule flange, i.e. the portion near proximal end 717. Once an ampule 21 is extracted, spring 900 turns spool 898 and automatically brings the next ampule 21 into position at access opening 930. After the last ampule 21 has been extracted, cover 896 is removed so that ampule strip 909 can be removed and discarded. A new ampule strip 909 is then installed as described above. Position of the pull-cord at all times is an indicator of the number of ampules remaining in magazine 890 as the cord is stepwise pulled into the housing when ampules 21 are extracted. Auto-feed magazine 890 makes use of the handpiece easier, because the ampule access point (opening 930) is always at the same place and the funnel in the cover (e.g. conical) can guide the jaws into position. To allow for the unlikely case of magazine malfunction, a slot 932 in housing side wall 904 provides a manual feed option where the user can pull the strip to advance the next ampule 21 into position for retrieval by the handpiece.

Figure 15:
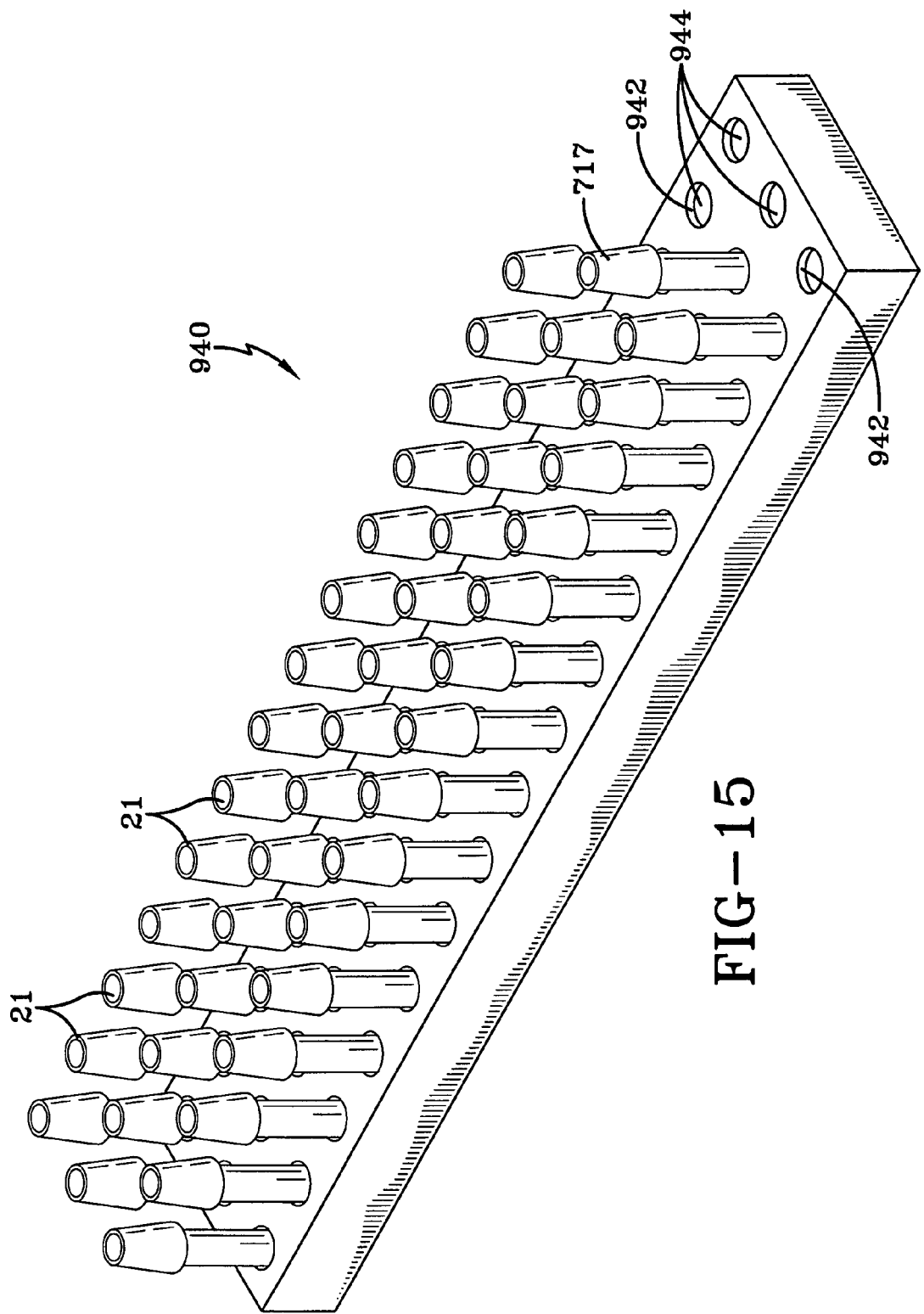
FIG. 15 is a pictorial view of ampules according to the invention located in a tray or crate assembly.

FIG. 15 illustrates the ampules housed in a crate assembly rather than the magazine structure described above. Accordingly, a crate 940 is provided which is made of cardboard, plastic or other appropriate material, which has a series of orifices 942 defining the entrance to receptacles 944 for receiving distal ends 716 of ampules 21 with proximal ends 717 extending from receptacles 944 for engagement by jaws of an appropriate handpiece. While this is the least expensive way to manage ampules 21, it is also the most likely to risk contamination and/or accidental spilling onto the floor.

Figure 16:
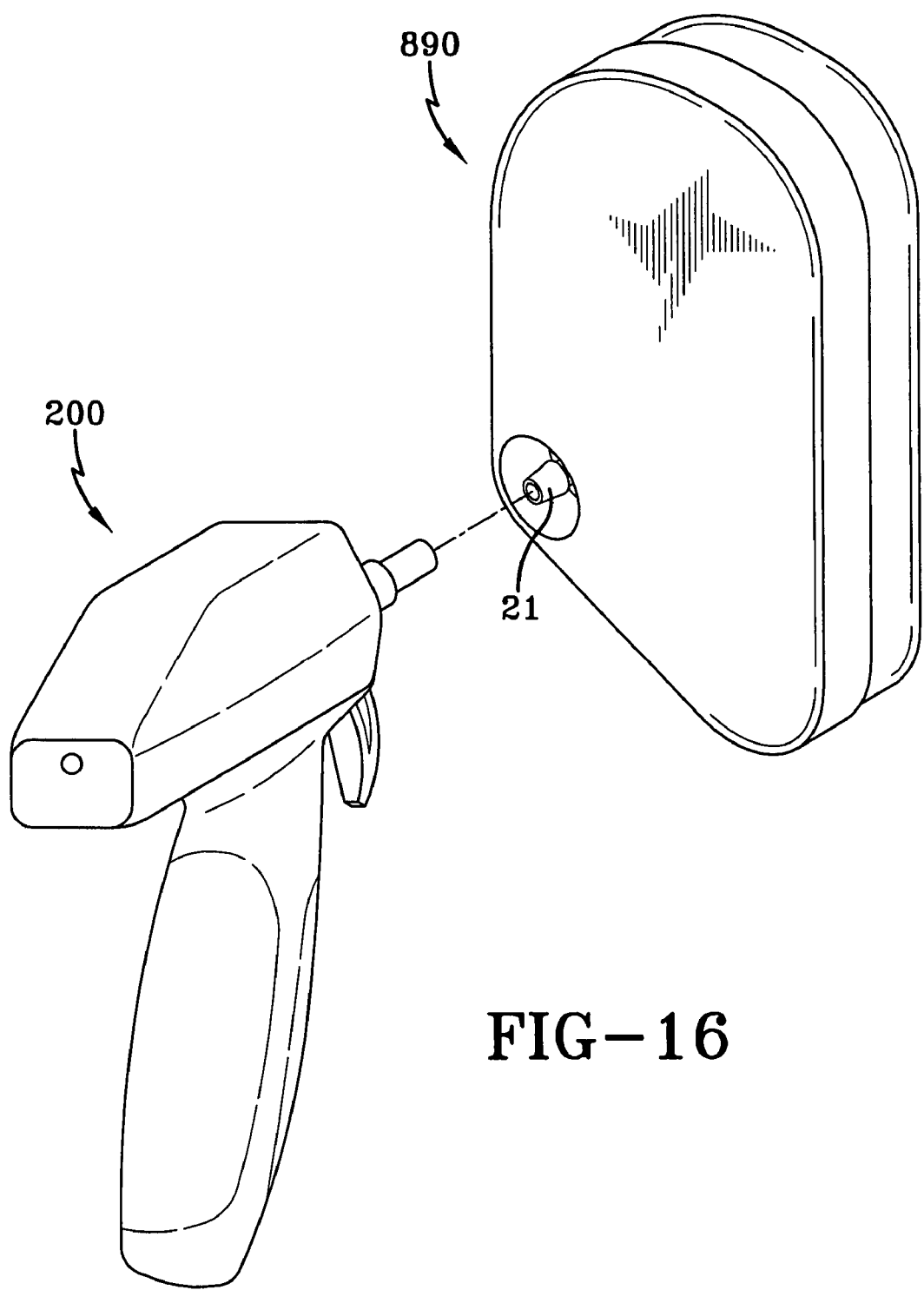
FIG. 16 is a pictorial view of the second embodiment of the invention shown in FIG. 2 retrieving a filled ampule from a rotating auto-feed magazine as shown in FIGS. 14a and 14b.

FIG. 16 illustrates an ampule 21 being extracted from auto-feed magazine 890 (FIG. 14) by injector 200 shown in FIG. 9. Ampule 21 could also be grabbed and extracted from folding magazine 820 (FIG. 13) or crate 940 (FIG. 15) with the same injector jaw assembly.

Figure 17:
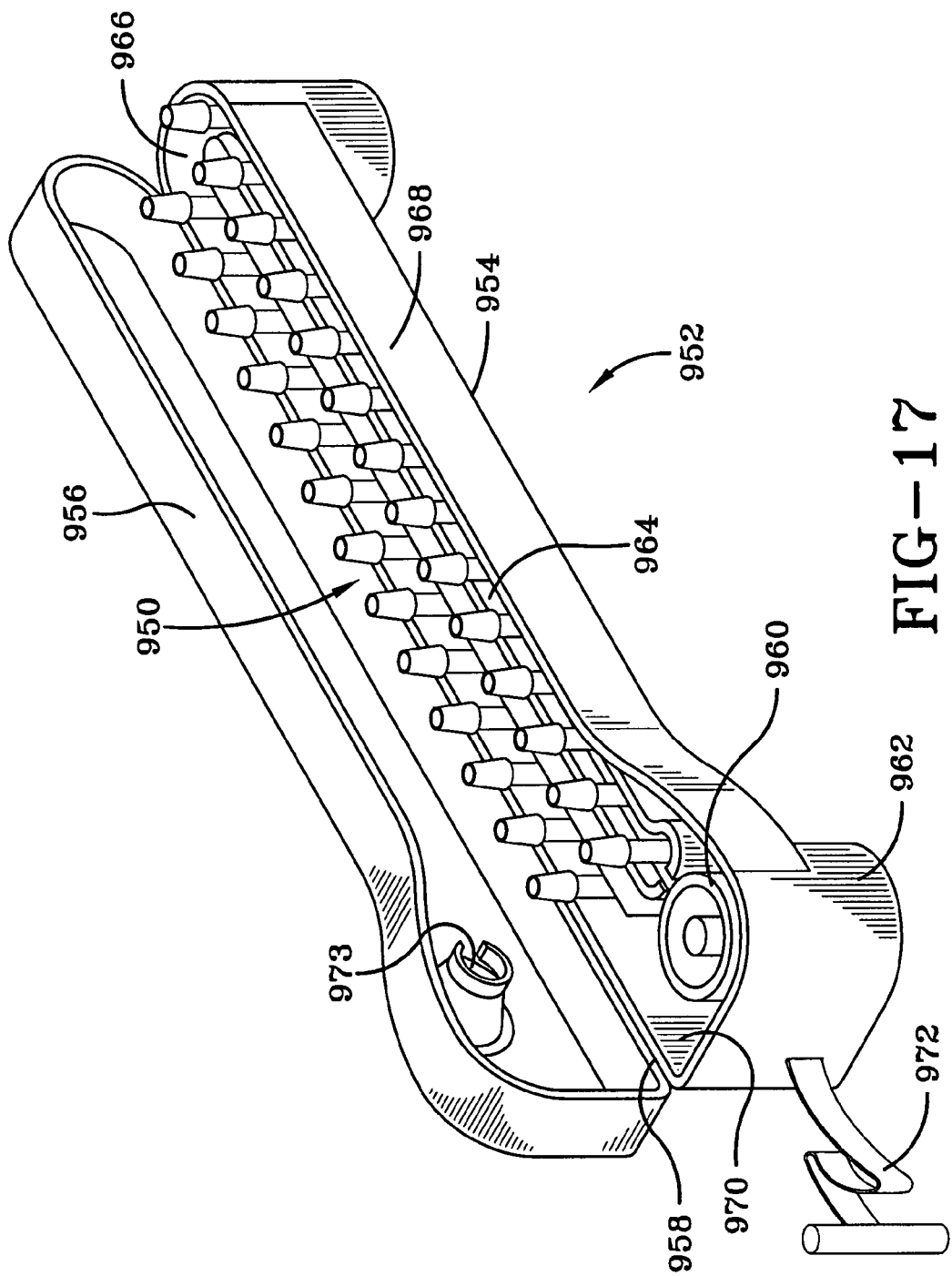
FIG. 17 is a pictorial view of another embodiment of the magazine portion of the invention showing a linear auto-feed magazine with an open cover.

FIG. 17 illustrates an in-line version of auto-feed magazine 890 shown in FIG. 14 and is geometrically similar to stationary magazine 820 shown in FIG. 13*d*. This in-line type magazine is the preferred embodiment in some cases because it reduces the amount of handling of the ampule strip, i.e., the packaging alignment is similar to the way it will be inserted into the filling station, and after that, into the magazine itself. This is easier and faster than trying to coil the ampule strip for use with the rotating magazine shown in FIGS. 14*a* and 14*b*. The in-line magazine is also easier to hold and equally convenient for wrist mounting if so desired. Thus, FIG. 17 shows in-line magazine 950 having a housing 952 comprised of a base 954 and a cover 956 connected to base 954 by an integral hinge 958. A spring wound take-up spool 960 (using negator spring 900) is disposed in an appropriately figured compartment 962 of housing 952. A longitudinally extending dividing wall 964 extends between compartment 962 and an end 966 of housing 952. A path for an ampule strip is defined between the opposite side surfaces of dividing wall 964 and the inside surfaces of opposing side walls 968, 970 of base 954. An ampule strip such as strip 800 in FIG. 12*a* could be used. It extends from a base end and extends to a connecting end attached to spool 960. A nylon pull-cord 972 for winding up negator spring 900 is shown in this FIG. 17, and is the same as that described above for magazine 890 in FIGS. 14*a*, 14*b*. In both auto-feed magazines 890, 950, the housing can also be transparent for a visual appraisal of the number of ampules remaining. A funnel-shaped opening 973 is provided for presenting the proximal end 717 of ampules 21 for grasping by the jaws of an injector.

Figure 18A:
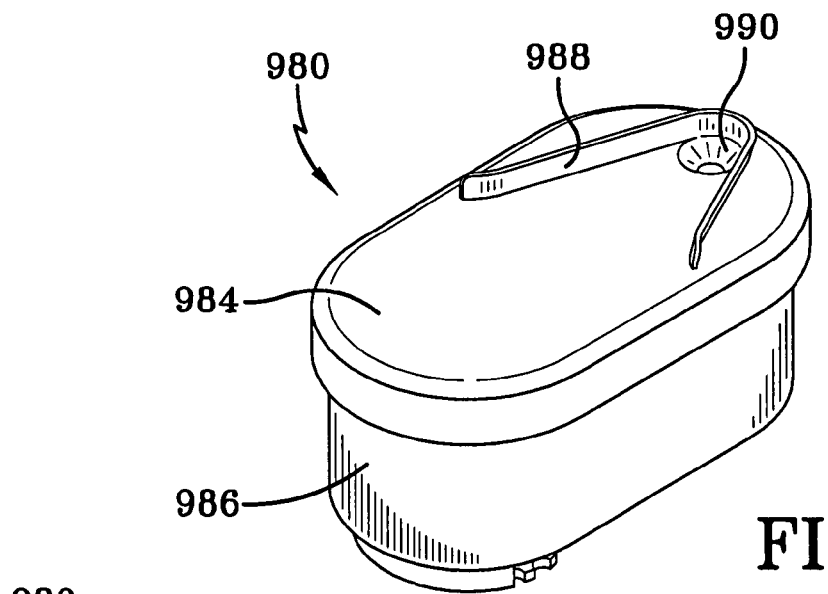
FIG. 18a is a pictorial view of another embodiment of the magazine aspect of the invention showing a rotatable auto-feed magazine with an improved structure for ampule retrieval.

FIG. 18*a* is another embodiment of the rotating auto-feed magazine. However, rotating auto-feed magazine 980 as shown has a housing with a cover 984 and a base 986. Cover 984 has a set of V-like rails 988 to virtually guide the injector nose into a funnel-shaped opening 990 where an ampule 21 appears for being grasped or retrieved with little or no visual contact by the user. For this reason, this embodiment is called a "noseeum" model; however, ampules 21 are grabbed by the jaw assembly the same as that described for the other magazine embodiments. It is noted that the "noseeum" feature is very important in high-speed procedures where it was found that delivery efficiency is greatly improved when the vaccinator is able to keep his/her eyes on the next patient rather than looking around for the next ampules 21.

Figure 18B:
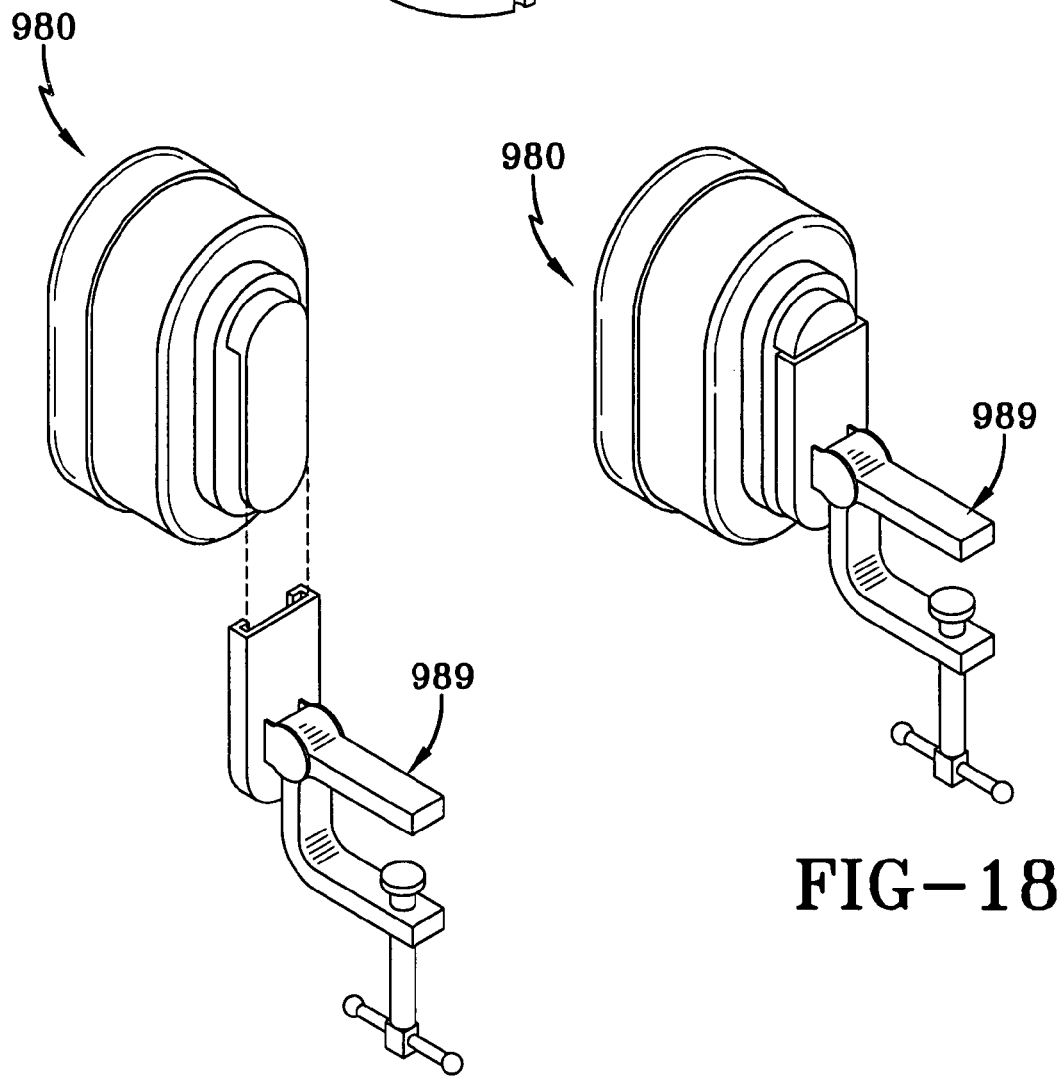
FIGS. 18b and 18c are views of the magazine shown in FIG. 18a in two mounting modes.
Figure 18C:
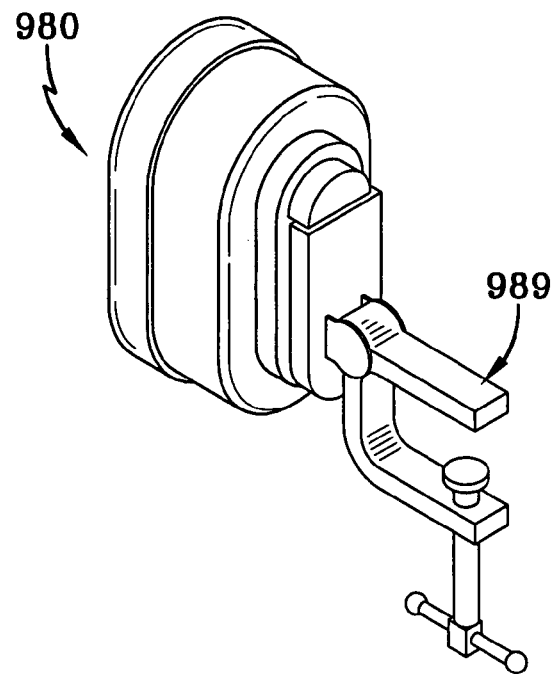

FIG. 18*b* illustrates magazine 980 in the released position from a mounting bracket 989, and FIG. 18*c* shows magazine 980 in the secured position in the mounting bracket 989. Mounting bracket 989 can be any appropriate bracket in the market.

Figure 19:
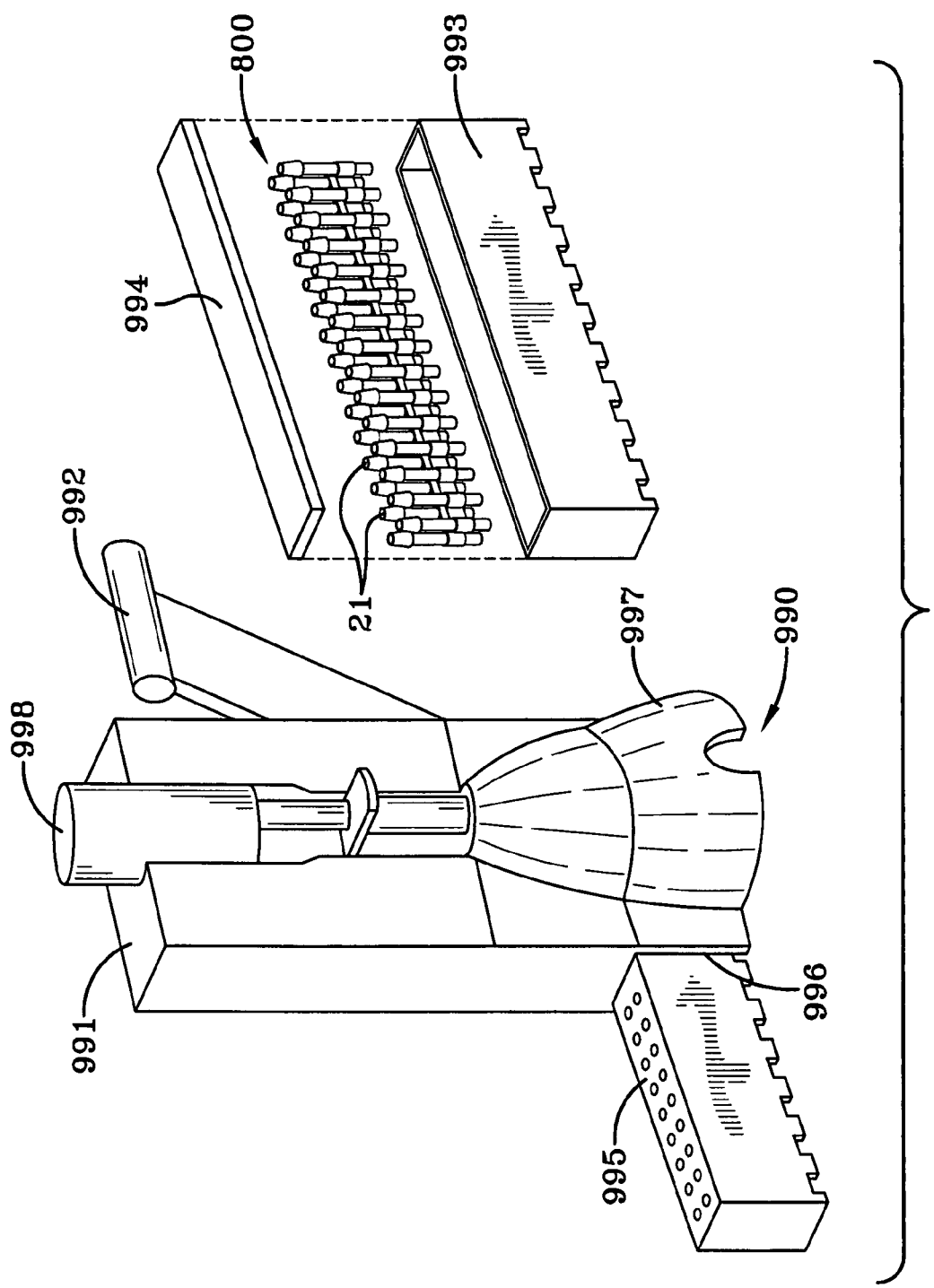
FIG. 19 is a pictorial view of a filling station according to the invention in partially exploded form.

FIG. 19 is an illustration of an ampule filling station 990 described above and will be included in injection kit 10 of FIG. 1. The purpose of filling station 990 is to accelerate the ampule fill rate. It could have a fill rate capacity in excess of 600 ampules per hour in order to keep up with patient throughput, or several filling stations with slower fill rates could be used simultaneously. A more likely scenario would be to use a slower fill rate filling station to pre-fill a large quantity of ampules before the start of vaccine administration. It is preferred that each ampule be addressed individually in a serial manner (as opposed to collectively in a parallel manner) to minimize maintenance/cleaning of the fluid path, reduce the chance of entrapping air bubbles, and reduce the possibility of contamination.

Filling station 990 includes a housing 991 and a manual fluid transfer handle 992. A magazine 993, which could be one of those discussed above, receives ampules 21 on a strip, such as ampule strip 800 shown in FIG. 12a. A shroud 994 is used to cover magazine 993 in order to reduce the likelihood of contamination. After magazine 993 housing empty ampules is inserted into the filling station at access port 997, injectate is forced into ampules 21 one by one upon the actuation of handle 992, which effects the filling of ampules 21 from injectate contained in syringe 998. The full magazine 995 exits the filling station at an exit 996 of filling station 990. The filled magazine 995 is again covered with a shroud 994 when it exits from filling station 990.

In an alternate embodiment, ampules can be provided in strips 800 that interface with filling station 990 directly. After being filled in much the manner as described above, strips 800 of filled ampules may then be placed immediately into magazine 993 or placed into cold storage to be installed in magazines just before use. While considering the various means for filling ampules 21 for mass immunization campaigns, and as mentioned above, the assumption is made that the vaccine is available in a 50-dose vial of lyophilized vaccine with the associated 30 ml vial of diluent. Single-dose or ten-dose vials may also be used, but the increased frequency of swapping vials will slow the overall filling process accordingly. The possible means for filling include: 1) forcing injectate through output orifice 710 as illustrated with filling station 990 shown in FIG. 19, 2) forcing injectate through the piston (similar in nature to that discussed below with reference to FIG. 20a, which refers to the use of lyophilized vaccine), and 3) pulling injectate through orifice 710 by drawing on the piston. Use of a piston to facilitate filling from a filling station (as opposed to forcing the vaccine in through the orifice when using the filling station) poses several problems. The small diameter of the piston (0.186 in, 4.72 mm), coupled with the lack of an ampule plunger in the injection system disclosed, makes it very difficult to create an appropriate interface to the filling station. The precision needed to interface with a smaller component could very well lead to problems in the rougher treatment expected in the field. This concept was therefore not included in filling station 990 of FIG. 19 as discussed above, but it does fall within the scope of the invention. The orifice at distal end 710 of ampule 21 provides for a more user-friendly interface due to the increased outside diameter of ampule 21 (0.375 in, 9.53 mm). Filling station 990 therefore preferably uses distal end 710 of ampule 21. Forcing the injectate into ampule 21 by use of a large syringe 998 as shown in FIG. 19, or by pressurizing the vial containing the reconstituted vaccine have all been considered. Pumping air into the vial (i.e., avoiding transfer of syringe 998) to pressurize the contents could be accomplished via a simple ball type pump (bulb) such as that found on a sphygmomanometer or via a mechanically actuated syringe pump. A more complicated system utilizing a motor driven pump, with manual override, is possible but would add cost, weight and complexity to the portable system. The main difficulty in using the vial comes in the valving required to control flow of air into the vial and flow of injectate out of the vial. In addition, how to control and monitor the pressure within the vial is at issue. The complexity of valving, coupled with the need for pressure control, favors a standard large syringe 998 as a solution for filling the ampules, and this is what is shown in FIG. 19. The syringe requires no valving, external pressurization, or pressure monitoring, to provide an accurate fill. In addition, and importantly, standard practice uses large syringes to mix the diluent with the lyophilized vaccine, and the same syringe 998 could then be used to then fill the ampules. A custom interface is provided for the syringe/vial interaction (i.e. for mixing diluent with lyophilized vaccine and for drawing mixed vaccine into syringe 998), or users could continue using standard needles to mix vaccine and to draw vaccine from the vial into the syringe. When filling ampules 21 from the syringes, advancement of the syringe plunger is accomplished via a simple lever action 992, or alternatively, a more, complicated motor driven means. Many of these issues were addressed when settling on the filling station of FIG. 19 and have been eliminated with the use of ampules 21 that are pre-filled with liquid vaccine as described, or much better, the lyophilized pre-filled ampules 21 as described for FIGS. 20a-20f below.

The series of ampule and magazine configurations illustrated in FIGS. 20a-20f are directed to the very important concept of the vaccine/medication manufacturers pre-filling the ampules prior to shipping them to the user. Pre-filling provides the promise for numerous improvements in some very important healthcare concerns, especially so in campaigns for mass immunization. Two of the most difficult considerations are time and sanitation, both of which are nicely addressed with the concepts disclosed. Time for preparation is a crucial factor for an immunization campaign in the difficult conditions often found in third world countries, and sanitation is virtually non-existent in some of these situations where misuse and mishandling runs rampant. This is especially true when it comes to handling the syringes and vaccine both before and after the injections are given.

The concepts found in FIGS. 20a-20f also address the problems that have long existed for pre-filled ampules. Plastic, for example, has long been banned for vaccine storage because of the possibility of leaching. While recent findings indicate that some of the higher-grade medical plastics may be satisfactory for long-term storage for vaccines, final approval remains to be seen; consequently, the concepts described in FIGS. 20a-20f deal with both plastic storage and the long-accepted means of storing in glass. The mixing ampules shown in FIGS. 20a-20f illustrate both a one-way valve and a frangible interface to provoke the mixing action; however, it has been shown that a one-way valve as shown in FIG. 20a with a small retaining pressure, will be effective for allowing the mixing action in place of a frangible interface as shown in the other figures, i.e., FIGS. 20d, 20e and 20f. It is also noted that in each of the diagrams shown in FIGS. 20a-20f, the lyophilized vaccine is shown as a small pill-type member for illustrative purposes; however, in reality, the vaccine will totally fill the space to assure a minimum of air in the compartment. By the same token, while it has been pointed out in earlier discussion that filling the ampules through the front end with liquid vaccine will virtually eliminate the introduction of air into the injectate chamber, the same is not true for the case of pre-filled lyophilized vaccine where a very small amount of air will inevitably exist; consequently, following the mixing action for each of these cases, some form of minimal venting may be needed.

FIG. 20a illustrates an ampule 1000 that contains lyophilized vaccine 1001 and its diluent, the two being separated by a piston 1002 having a piston head 1004 with a one-way valve 1006 in the direction of an exit nozzle 1018. The embodiment shown uses umbrella valve 1006 that will open (as shown in dotted lines) when piston 1002 is pulled vertically downward in the figure, wherein a diluent 1010 is forced upward, through the fluid flow path channel, past the valve, and into the lyophilized portion of the chamber for immediate mixing. Piston 1002 has a ring seal 1012 for sealing against fluid flow around the periphery of piston 1002. The injection is given by first removing a cap 1016 that seals an orifice 1018, slightly advancing the now sealed piston head 1004 to expel any air, and then fully pushing piston 1002 forward for the injection, wherein umbrella valve 1006 will seal throughput ports 1020 that were used for the mixing action. Cap 1016 shown on exit port 1018 is needed to prevent air from being pulled into ampule 1000 and must be removed to vent air and before an injection is given. Piston 1002 has a piston rod 1022 which is designed so that the MIT injector ram can optionally grab and pull it back during motor reversal when arming occurs. A seal 1024 is provided around an orifice 1026 in ampule 1000 to prevent leakage through orifice 1026. Alternatively, rod 1022 can be eliminated if a small piece of magnetic material, such as a magnetic disk, is attached to the proximal side 1028 of piston head 1004. A strong magnet on the injector ram (such as ram 403) will make contact with the metal disk when ampule 1000 is inserted; consequently, piston head 1004 will follow the ram in the reverse direction when arming occurs. After an injection, piston 1002 must be locked in the forward position as described earlier (see FIG. 10*a*), thus allowing a small reverse jog of the ram to separate the two for sanitary disposal.

FIG. 20*b* has only lyophilized medication 1001 in the forward or distal part of ampule 1000. In this case, diluent 1010 is forced into exit nozzle 1018 from a filling station, while at the same time forcing piston 1002 to the proximal end of ampule 1000. As before, the need for venting is likely, and a rapid forward push on piston 1002 will provoke the injection.

FIG. 20*c* again has lyophilized vaccine 1001 in the forward part of ampule 1000; however, in this case, an appendage 1030 containing diluent 1010 is attached to exit nozzle 1018 with an appropriate seal 1032. When an appendage piston 1034 is forced downward, diluent 1010 will flow into the chamber for immediate mixing while simultaneously pushing injector piston 1002 to the proximal end of ampule 1000. This model is ideally suited to the mixing magazine system described in FIG. 20*e* below.

FIG. 20*d* has both lyophilized vaccine 1001 and diluent 1010 in an appendage 1036 connected to the front end; however, the two are separated by a very thin, frangible interface 1038, or alternatively, a one-way valve. As soon as pressure is applied to an appendage piston 1040 and interface 1038 is broken, diluent 1010 is forced into the lower chamber to provoke immediate mixing in appendage 1036, and at the same time, forcing the mixed fluid through nozzle 1018 to force injection piston 1002 to the proximal end of ampule 1000. This technique is also ideally suited to the mixing magazine of FIG. 20*e*.

FIG. 20*e* illustrates a complete mixing/shipping magazine that houses a multitude of pre-filled ampules. This technique could be housed in a lid for the stationary folding magazine and/or the auto-feed magazines described earlier. As such, the force needed to provoke the mixing action will require that the lid be collapsible into the lower stationary portion of the magazine. This type of magazine will ideally serve as a shipping container to further reduce the risk of contamination due to ampule handling, the need for which is virtually zero. The appendage for each ampule is similar to that described for FIG. 20*d*; however, in this case, the appendage is shown as a bellows assembly. Either type of collapsible appendage is suitable for exercising the techniques described.

Still referring to FIG. 20*e*, a filling system 1100 is shown. It has a force transfer member 1102 for collapsing pleated walls 1104 of storage unit 1103 to collapse a chamber 1106 holding diluent 1010 above a frangible interface 1138, and lyophilized medication 1001 below interface 1138. This applies to each of N filling stations filled by the operation of member 1102. Each ampule 1000 has a body portion with piston 1002 having wall engaging seals 1012. Storage unit 1103 is connected to exit nozzle 1018 having a seal 1032 to prevent leakage. Upon the application of sufficient downward force on member 1102, the mixing diluent 1010 and lyophilized medication 1001 flow through exit orifice 1018, forcing piston 1002 downward as shown by the arrow to fill the ampule. A cap could optionally be applied over nozzle or orifice 1018 to close ampule 1000 until an injection is made.

FIG. 20*f* illustrates an ampule 1200 that contains a lyophilized vaccine 1202 and its diluent 1204, and in that regard is similar to FIG. 20*a*. However, in this case, the separation is a very thin, inexpensive frangible barrier 1206 that eliminates the cost of an appendage and/or the piston with the one-way valve. A piston 1210 having an annular seal 1212 is provided. Barrier 1206 is held in place by a sliding seal 1208 which is used to properly locate frangible barrier 1206 in ampule 1200. Force on ampule piston 1210 will cause barrier 1206 to fracture (or a one-way valve to open) and the mixing action occurs. As soon as mixing is complete and the ampule is full of liquid, a sealing cap 1214 can be removed, whereupon the sliding seal 1208 on barrier 1206 will move with piston 1210 as it reaches barrier 1206 and completes the injection transition through exit port 1216.

While the examples described for the procedures depicted in FIGS. 20*a*-20*f* illustrate a direct pushing force to provoke the mixing action, a twisting motion for advancing a threaded interface could also be used to facilitate the mixing action.

Finally, it should be noted that the conventional jet injector orifices shown in all of the above descriptions can be replaced with a perforator exit nozzle as disclosed in U.S. Pat. No. 6,056,716. Perforator delivery has been extensively experimented with by the inventors over a number of years and has been shown to allow for lower jet pressure, painless delivery because the jet stream begins from just inside the skin, which eliminates the need for the high-speed jet velocity required for crossing the barrier of fully exposed skin. Protection against sharps injury to the healthcare workers remain a concern; however, safety is realized by hiding the perforator before the injection, and having the injector itself destroy the perforator after the injection. Several methods are shown to be effective, one being where the perforator is extended through a tight fitting exit port of a compressible, protective front end that becomes an off axis shield after the perforator is drawn back into the protective housing, i.e., as described for FIGS. 8*a* and 8*d*. In another approach, an off-axis, exit hole on a rotatable disk located at the exit nozzle will automatically rotate after the injection to therefore crush and disable the perforator to the point where it is virtually impossible to do any damage. Another tremendous advantage for using this low-pressure technique is the very low cost for a thin-walled ampule. The inventors have shown over the course of many years of experimentation that pressures of anywhere from 200 to 1000 psi are effective for virtually any type of injection, the preferred pressure depending on the patient, location for the injection and the required depth for the delivery (i.e., intradermal, subcutaneous or intramuscular). Because of this, the use of low cost, thin-walled glass is also possible, since the inventors have also shown that the low cost glass ampules that are readily available will not fracture until exposed to pressures in excess of 1500 psi. Consequently, glass ampules for housing the vaccines for long term storage is a realistic goal for the pre-filled techniques described if perforator delivery is used.

The invention has been described in detail, with particular emphasis on the preferred embodiment thereof, but variations and modifications within the spirit and scope of the invention may occur to those skilled in the art to which the invention pertains.

What is claimed is:

1. A hypodermic injector for injecting fluid from a respective ampule loaded in said injector from a plurality of ampules in sequence, each ampule having a moveable piston, at least one chamber and an exit orifice from said at least one chamber, the at least one chamber being alternatively in a sealed condition for containing injectate and an empty condition when the injectate has been discharged from the ampule through said exit orifice, the respective ampules being operable by said hypodermic injector without the necessity of human contact with the respective ampules before or after an injection, said injector comprising:

a grasping mechanism having a grasping condition for grasping the respective ampules and holding the respective ampules to receive an injectate discharge force, and an open condition for releasing the respective ampules, said grasping mechanism comprising:
   gripper jaws having both a closed position for gripping the respective ampule and an open position;
   at least one jaw expansion spring for outwardly biasing said gripper jaws in the open position; and
   a gripper jaw capture sleeve having a holding position for holding said gripper jaws in the closed position against the biasing of said at least one jaw expansion spring, and a releasing position for enabling said gripper jaws to assume the open position;

a plunger device movable from a set condition to a discharge condition for applying discharge force to the moveable piston in the respective ampule when the respective ampules are in the sealed condition gripped in said gripper jaws to eject injectate from the respective ampules through said exit orifice to render the ampule in the empty condition;

a first biasing device having both a cocked condition for storing a biasing force in said device and a released condition, said first biasing device applying discharging force to said plunger device to move said plunger device from the set condition to the discharge condition in response to the movement of said biasing device from the cocked condition to the released condition;

a first cocking mechanism for moving said first biasing device from the released condition to the cocked condition;

a release mechanism actuatable for releasing said first biasing device from the cocked condition to the released condition to effect the movement of said plunger device from the set condition;

an ejector mechanism for ejecting an empty ampule from said grasping mechanism when said ejector mechanism is in the open condition, wherein said ejector mechanism comprises:
   a gripper jaw sleeve releasing mechanism for causing said gripper jaw capture sleeve to move to the releasing position to enable said gripper jaws to assume the open position;
   an ejection sleeve movable from a set condition to an ejecting condition for ejecting an ampule from said gripper jaws when said gripper jaws are in their open position without requiring the user of said injector to touch the ampules;
   a second biasing device releasable from a cocked condition to a released condition to drive said ejection sleeve to the ejecting condition to eject the ampule; and
   a second cocking mechanism for moving said second biasing device from the released condition to the cocked condition.

2. A hypodermic injector according to claim 1 wherein said second cocking mechanism places said second biasing device in the cocked condition in response to the loading of an ampule into said injector.

3. A hypodermic injector according to claim 1 wherein said ejector mechanism further comprises:
   a release member for discharging said second biasing device from the cocked condition, said release member being operable from the group consisting of manually operable and automatically operable.

4. A hypodermic injector according to claim 1 and further including a motor having a drive shaft operatively connected to said first cocking mechanism, said drive shaft being rotatable in one direction to cause said first cocking mechanism to assume the cocked condition from the released condition to move said first biasing device from the released condition to the cocked condition, and automatically rotatable in a reverse direction to reset said drive shaft for the next operation to cause said first cocking mechanism to assume the cocked condition.

5. A hypodermic injector according to claim 1 wherein said grasping mechanism assumes the open condition when no ampule is grasped by said grasping mechanism, and wherein said grasping mechanism includes a disabling device for disabling said plunger device from moving from the set condition when no ampule is in said grasping mechanism and said grasping mechanism is in the open condition.

6. A hypodermic injector according to claim 1 wherein said hypodermic injector further includes at least one of a remote electric motor and a manual mechanism, and a coupling mechanism for operatively coupling at least one of said motor and said manual mechanism to said first cocking mechanism, and a handpiece with a housing for containing said grasping mechanism, plunger device, first biasing device, first cocking mechanism, release mechanism, ejector mechanism and second cocking mechanism.

7. A hypodermic injector according to claim 1 wherein each of said ampules has an outer wall with said at least one chamber for containing the injectate, a proximal end and a distal end with the exit orifice in the distal end through which injectate can flow, the at least one chamber extending between the distal end and the proximal end, wherein said piston moves from the proximal end towards the distal end under the influence of said first biasing device to force injectate from the at least one chamber through the exit orifice to deliver an injection, wherein said injector further includes a motor having a drive shaft operatively connected to said first cocking mechanism and said piston, said drive shaft being rotatable to cause said first cocking mechanism to assume the cocked condition from the released condition while simultaneously drawing the piston from the distal end of the ampule to the proximal end of the ampule to enable filling of the ampule with the injectate through the orifice during the cocking procedure to draw injectate into the ampule in preparation for an injection.

8. A hypodermic injector according to claim 1 and further including a magazine for sequentially providing one of said respective ampules to be grasped by the grasping mechanism from ampules held in sequence in said magazine, said magazine comprising:
a housing having a holding region for holding ampules, and for making said one of said respective ampules accessible to said grasping mechanism for extraction of said respective ampules from said holding region in sequence.

9. A hypodermic injector according to claim 8 wherein said housing comprises:
access orifices having access surfaces defining an opening for said one of said respective ampules wherein said grasping mechanism can grasp one of said respective ampules from said orifice and withdraw the ampule from said magazine.

10. A hypodermic injector according to claim 1 wherein said first biasing device is at least one spring having a biasing force sufficient to drive said plunger device with enough energy to eject injectate at jet stream velocity.

11. A hypodermic injector according to claim 1 and further including a perforator operatively connected to the ampule for injecting fluid injectate in response to the movement of said plunger device from the set condition to the discharge condition, said first biasing device driving said plunger device in an increasing manner during an injection process, to increase the discharge force applied by said plunger device to increase the pressure in the injectate fluid to increase the depth of injection in a body being injected as compared to the depth of injection by an injector having a diminishing discharge force.

12. A hypodermic injector according to claim 1 wherein said ampule further comprises:
a piston structure for disabling said ampule upon completion of an injection with said ampule, said hypodermic injector comprising apparatus for driving said piston structure beyond the injection stroke to destroy said piston at said orifice at the completion of an injection thus rendering said ampule incapable of reuse.

13. A hypodermic injector according to claim 11 wherein said perforator at the end of said orifice for penetrating the skin of a body being injected controls the injection depth and reduces the force required to make the injection.

14. A hypodermic injector according to claim 13 and further comprising an ampule disabling structure for disabling said ampule upon completion of an injection with said ampule, said ampule disabling structure comprising a disabling device substantially covering said perforator for disabling said ampule after an injection has been made using the ampule.

15. A hypodermic injector according to claim 14 wherein said disabling device is a collapsible cover for said perforator having a weakened wall which collapses upon the rendering of an injection to render said perforator inaccessible.

16. A hypodermic injector according to claim 13 wherein said perforator is the thickness of skin of the person or animals to be injected at the place of injection, the animals include dogs, cats, pigs, cows, horses, elephants, chickens, turkeys, roosters, geese, lobsters, crabs, goats, camels and sheep.

17. A hypodermic injector according to claim 16 wherein said perforator has a length of from 1.0 mm to 12.7 mm.

18. A hypodermic injector and ampule according to claim 1;
said ampule comprising a body portion having inside surfaces defining a chamber, said body portion having an orifice extending to said chamber at one end of the body portion defining a path for injectate during an injection;
a piston in said chamber extending between the inside surfaces of said body portion;
a portion of said chamber on one side of said piston for initially holding lyophilized medication;
a portion of said chamber on the other side of said piston for holding a diluent for the lyophilized medication;
structure for enabling flow and mixture of the diluent with the lyophilized medication in response to movement of said piston to prepare injectate to be discharged from said ampule; and
structure for disabling said ampule upon completion of an injection with said ampule.

19. An ampule according to claim 18 wherein said structure comprises a one-way valve on said piston for opening when the piston moves in a direction away from said orifice, and closing in response to movement of said piston towards said orifice to effect an injection.

20. A hypodermic injector and ampule according to claim 1;
said ampule comprising a body portion having inside surfaces defining a chamber, said body portion having an orifice extending to said chamber at one end of said body portion for discharging injectate during an injection; and
a piston located in said chamber extending between said inside surfaces and defining a cavity between said piston and said orifice for receiving lyophilized medication;
said orifice being able to receive diluent under pressure for mixing with the lyophilized medication in said cavity to form an injectate; and
said piston being movable away from said orifice in response to the entry of diluent into said cavity to enlarge the size of said cavity.

21. A hypodermic injector according to claim 6 wherein said first cocking mechanism is a selected one of the group consisting of a draw rod and a push rod, said selected one of the group consisting of a draw rod and a push rod being moved a predetermined distance to set the injection spring, and at least one of said manual mechanism or electrical motor including a device for gripping the draw rod or pushing said push rod for moving said plunger device by the predetermined distance to set the injection spring.

22. A hypodermic injector according to claim 1 having said ampule for holding an injectate supply, said ampule having an injectate entrance and discharge orifice, and an injectate holding chamber, wherein said ampule includes a plunger in said chamber, said chamber receiving injectate from a reservoir with external positive pressure to force said plunger away from said orifice to effect the transfer of injectate fluid from the reservoir to said chamber, said ampule receiving injectate into said ampule without allowing air to be forced into said chamber.

23. A hypodermic injection system according to claim 1 comprising:
a handpiece for receiving said ampule containing an injectate, said handpiece having an ampule holding device for holding said ampule and an injectate discharge device actuable for effecting the discharge of injectate from said ampule held by said ampule holding device, a personally-operated arming apparatus remote from said handpiece, and an electrical or manual connector for operably connecting said arming apparatus and said injectate discharge device for arming said injectate discharge device in response to operation of said personally-operated arming device.

24. A hypodermic injector according to claim 1 wherein said first biasing device moves said plunger device in an increasing manner during an injection process, to increase the discharge force applied by said plunger device to increase the pressure in the injectate fluid to increase the depth of the injection in a body being injected as compared to the depth of injection by an injector having a diminishing discharge force.

25. A hypodermic injector and magazine according to claim 8, wherein said magazine is configured as a crate assembly for holding said ampules for withdrawal of ampules held in the crate assembly by said hypodermic injector ampule-grasping mechanism in an injection procedure, the ampules comprising a generally cylindrical body portion with a relatively narrow diameter extending from a forward portion towards a rearward portion and a wider portion having a peak near the rearward portion and a tapered rearwardly-extending surface extending from the peak to the rearward end of the ampule, said crate assembly comprising:
   a support surface having a series of orifices defined by orifice surfaces having diameters slightly larger than the diameters of the forward portion of the ampule to provide sufficient contact between the respective orifice surfaces and the held ampules for holding the ampules with the forward end in a respective orifice to prevent the ampules from falling out of the orifices during ordinary use of said crate assembly during an injection procedure, and the wider portion of the ampule extending from said orifices in positions to be grasped by a hypodermic injector having an ampule-grasping mechanism.

26. A hypodermic injector and ampule according to claim 1, said ampule comprising:
   a body portion with a proximal end, a distal end and a longitudinal axis extending between said proximal end and said distal end, said body portion having a chamber having a relatively large opening in said proximal end and terminating before said distal end, and further having a relatively small orifice extending between the termination of said chamber and said distal end; and
   a slidable spool located in said chamber between said piston and said proximal end, and a spring device associated with said spool locking said spool in said chamber against movement towards said proximal end;
   said piston being slidable in said chamber from a position adjacent said orifice to said spool in response to the flow of injectate under pressure through said orifice; and
   said spool forcing said piston towards said orifice by the high-speed impact of a plunger against said spool to force injectate through said orifice to effect an injection.

27. A hypodermic injector for injecting fluid from a respective rigid ampule loaded in said injector from a plurality of ampules in sequence, each ampule having a moveable piston, at least one chamber and an exit orifice from said at least one chamber, the at least one chamber being alternatively in a sealed condition for containing injectate and an empty condition when the injectate has been discharged from the ampule through said exit orifice, the respective ampules being operable by said hypodermic injector without the necessity of human contact with the respective ampules before or after an injection, said injector comprising:
   a grasping mechanism having a grasping condition for grasping the respective ampules and holding the respective ampules to receive an injectate discharge force, and an open condition for releasing the respective ampules, said grasping mechanism comprising:
      gripper jaws having both a closed position for gripping the respective ampule and an open position;
      at least one jaw expansion spring for outwardly biasing said gripper jaws in the open position; and
      a gripper jaw capture sleeve having a holding position for holding said gripper jaws in the closed position against the biasing of said at least one jaw expansion spring, and a releasing position for enabling said gripper jaws to assume the open position;
   a plunger device movable from a set condition to a discharge condition for applying discharge force to the moveable piston in the respective ampule when the respective ampules are in the sealed condition gripped in said gripper jaws to eject injectate from the respective ampules through said exit orifice to render the ampule in the empty condition;
   a first biasing device having both a cocked condition for storing a biasing force in said device and a released condition, said first biasing device applying discharging force to said plunger device to move said plunger device from the set condition to the discharge condition in response to the movement of said biasing device from the cocked condition to the released condition;
   a first cocking mechanism for moving said first biasing device from the released condition to the cocked condition;
   a release mechanism actuatable for releasing said first biasing device from the cocked condition to the released condition to effect the movement of said plunger device from the set condition;
   an ejector mechanism for ejecting an empty ampule from said grasping mechanism when said ejector mechanism is in the open condition, wherein said ejector mechanism comprises:
      a gripper jaw sleeve releasing mechanism for causing said gripper jaw capture sleeve to move to the releasing position to enable said gripper jaws to assume the open position;
      an ejection sleeve movable from a set condition to an ejecting condition for ejecting an ampule from said gripper jaws when said gripper jaws are in their open position without requiring the user of said injector to touch the ampules;
      a second biasing device releasable from a cocked condition to a released condition to drive said ejection sleeve to the ejecting condition to eject the ampule; and
      a second cocking mechanism for moving said second biasing device from the released condition to the cocked condition.

* * * * *